(12) United States Patent
Kodama et al.

(10) Patent No.: US 6,605,409 B2
(45) Date of Patent: Aug. 12, 2003

(54) POSITIVE RESIST COMPOSITION

(75) Inventors: Kunihiko Kodama, Shizuoka (JP); Shinichi Kanna, Shizuoka (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 41 days.

(21) Appl. No.: 09/860,440

(22) Filed: May 21, 2001

(65) Prior Publication Data

US 2002/0006578 A1 Jan. 17, 2002

(30) Foreign Application Priority Data

May 22, 2000 (JP) ........................................ 2000-150217

(51) Int. Cl.$^7$ .......................... G03F 7/004; C07C 25/00; C07C 381/00; C07D 275/06
(52) U.S. Cl. ..................... 430/270.1; 430/914; 430/921; 430/922; 548/206; 548/211; 568/18; 568/30; 570/101; 570/182
(58) Field of Search .............................. 430/270.1, 914, 430/921, 922; 568/18, 30; 570/101, 182; 548/206, 211

(56) References Cited

U.S. PATENT DOCUMENTS 5,411,998 A * 5/1995 McArdle et al.

6,060,213 A 5/2000 Kodama

FOREIGN PATENT DOCUMENTS

| JP | 9-258435 | | 10/1997 |
| JP | 11-305439 | * | 5/1999 |

OTHER PUBLICATIONS

English Translation of JP 11–305439 May 1999.*

Patent Abstracts of Japan (JP 9–258435).

European Search Report dated Sep. 11, 2001.

* cited by examiner

*Primary Examiner*—Rosemary Ashton
(74) *Attorney, Agent, or Firm*—Sughrue Mion, PLLC

(57) ABSTRACT

A positive resist composition comprising (A) a compound generating a specific sulfonimide compound by irradiation with an actinic ray or a radiation and (B) a resin having a group, which is decomposed by the action of an acid to increase the solubility of the composition in an alkali developer. The resist composition has an improved resolving power and an improved process allowance such as exposure margin and the depth of focus in a lithographic technique using a light source of short wavelengths capable of super fine working and a positive chemically amplified resist.

32 Claims, No Drawings

POSITIVE RESIST COMPOSITION

FIELD OF THE INVENTION

The present invention relates to a positive photosensitive composition which is used for the production process of lithographic printing plates and semiconductors such as IC, etc., the production of circuit substrates such as liquid crystals, thermal heads, etc., and for other photofabrication processes.

BACKGROUND OF THE INVENTION

As a photosensitive composition which is used for the production process of lithographic printing plates and semi-conductors such as IC, etc., the productions of circuit substrates such as liquid crystals, thermal heads, etc, and other photofabrication processes, there are various compositions, and in general, photoresist photosensitive compositions are used and the photosensitive compositions are largely classified into two groups, i.e., a positive photosensitive composition and a negative photosensitive composition.

As one of positive photoresist photosensitive compositions, there is a chemically amplified type resist composition described in U.S. Pat. No. 4,491,628 and European Patent 249,139. The chemically amplified type resist composition is a pattern-forming material of forming an acid at a exposed portions by the irradiation of a radiation such as a far-ultraviolet light, etc., and by the reaction using the acid as a catalyst, changing the solubility of the exposed portions and the unexposed portions by the active radiation in a developer, thereby, forming a pattern on a substrate.

As such an example, there are a combination of a compound generating an acid by a photodecomposition and acetal or an O, N-acetal compound (Japanese Patent Laid-Open No. 89003/1973), a combination of a compound generating an acid by a photodecomposition and an ortho-ester or an amidoacetal compound (Japanese Patent Laid-Open No. 120714/1976), a combination of a compound generating an acid by a photodecomposition and an enol ether compound (Japanese Patent Laid-Open No. 12995/1980), a combination of a compound generating an acid by a photodecomposition and an N-acyliminocarbonic acid compound (Japanese Patent Laid-Open No. 126236/1980), a combination of a compound generating an acid by a photodecomposition and a polymer having an ortho-ester group at the main chain (Japanese Patent Laid-Open No. 17345/1981), a combination of a compound generating an acid by a photodecomposition and a tertiary alkyl ester compound (Japanese Patent Laid-Open No. 3625/1985), a combination of a compound generating an acid by a photodecomposition and a silyl ester compound (Japanese Patent Laid-Open No. 10247/1985), and a combination of a compound generating an acid by a photodecomposition and a silyl ether compound (Japanese Patent Laid-Open Nos. 37549/1985 and 121446/1985). Because the quantum yields of these combinations exceed 1, in principle, they show a high photosensitivity.

Similarly, as a system, which is stable with the passage of time at room temperature but is decomposed by heating in the existence of an acid to become alkali soluble, there are the combination systems of the compounds generating an acid by light exposure and the esters of a tertiary or secondary carbon (for example, t-butyl and 2-cyclohexenyl) or a carbonic acid ester compounds described in Japanese Patent Laid-Open Nos. 45439/1984, 3625/1985, 229242/1987, 27829/1988, 36240/1988, and 250642/1988, "Polym. Eng. Sce", Vol. 23, 1012(1983), "ACS. Sym.", vol. 242, 11(1984); "Semiconductor World", November 1987, page 91; "Macromolecules". Vol. 21, 1475(1988); "SPIE", Vol. 920, 42(1988), etc. These systems also have a high sensitivity and can become an effective system of using a light source having a short wavelength capable of super-fine working because the absorption in a far ultraviolet region is less.

The positive chemically amplified resist described above is largely classified into (i) a three-component system comprising an alkali-soluble resin, a compound generating an acid by a radiation exposure (photo-acid generator), and a dissolution-inhibiting compound to an alkali-soluble resin and having an acid-decomposable group and (ii) a two-component system comprising a resin having a group, which becomes alkali-soluble by being decomposed by the reaction with an acid and photo-acid generator.

In the positive chemically amplified resist of the two-component system or the three-component system, by the existence of an acid generated from the photo-acid generator by the exposure, after heat treatment, the resist is developed to obtain a resist pattern.

These positive chemically amplified resist can become the effective system for the short wavelength of light source capable of super fine working as described above, but further the improvement of the resolving power and the improvement of the process allowance such as the light exposure margin and the depth of focus have been desired.

In addition, in the above-described chemically amplified resist, a compound generating a strong acid such as a sulfonic acid (e.g., trifluoromethanesulfonic acid), hexafluorophosphoric acid, tetrafluoroboric acid, etc., is generally used as the compound generating an acid by photo-decomposition. However, when such a compound generating a strong acid is used, the acid-decomposable protective group is once decomposed by the acid catalyst and the composition become alkali-soluble, but there is a problem that because the acid catalyst generated is a very strong acid, the release protective group is re-bonded to the resin or causes the crosslinking of the resin, whereby the alkali-solubility of the exposed portions is lowered, the resolving power is deteriorated or the development residue occurs. Also, in the points of the process allowance such as the exposure margin, the depth of focus, etc., further improvement has also been required.

However, even the above-described techniques cannot sufficiently cope with the present fine work and there leaves room for the improvement of the resolving power and the improvement of the process allowance such as the exposure margin and the depth of focus.

SUMMARY OF THE INVENTION

An object of the present invention is to provide a positive resist composition having an improved resolving power and an improved process allowance such as the exposure margin and depth of focus in the lithographic technique using an exposure light source having short wavelength capable of super fine working and positive chemically amplified resist.

As the result of various investigations, it has been found that the above-described object can be attained by the positive resist composition of the invention having the following composition.

(1). A positive resist composition comprising:
(A) a compound generating a compound represented by the formula (I) below by irradiation with an actinic ray or a radiation; and (B) a resin having a group which is decomposed by the action of an acid to increase the solubility of the composition in an alkali developer:

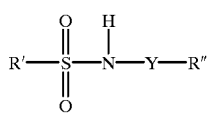
(I)

wherein, Y represents a single bond, —CO—, or —SO$_2$—; R' and R", which may be the same or different, each represents a straight chain, branched, or cyclic alkyl group which may be substituted, an aryl group which may be substituted, an aralkyl group which may be substituted, or a camphor group; R' and R" maybe bonded to each other to form an alkylene group, an arylene group, or an aralkylene group, thereby, the structure of the formula (I) may form a ring; and when Y is a —CO— group, R" may be a hydroxy group or an alkoxy group.

(2). The positive resist composition according to the above item (1), which further comprises (D) a compound having a molecular weight of not larger than 3000, which is decomposed by the action of an acid to increase the solubility in an alkali developer.

(3). The positive resist composition according to the above item (1), wherein the pKa of the compound represented by the formula (I) is in the range of from −5 to 5.

(4). The positive resist composition according to the above item (1), wherein the resin (B) is a resin containing repeating structural units represented by the following formulae (II) and (III)

(II)

(III)

wherein L represents a hydrogen atom, a straight chain, branched, or cyclic alkyl group which may be substituted, or an aralkyl group which may be substituted; Z represents a straight chain, branched, or cyclic alkyl group which may be substituted or an aralkyl group which may be substituted; and Z and L may be bonded to each other to form a 5- or 6-membered ring.

(5). The positive resist composition according to the above item (4), wherein Z of the formula (II) is a substituted alkyl group or a substituted aralkyl group.

(6). The positive resist composition according to the above item (1), which further comprises (F) a nitrogen-containing basic compound and (G) at least one of a fluorine atom containing surfactant and a silicon atom containing surfactant.

(7). The positive resist composition according to the above item (1), wherein the compound (A) is a compound having a structure represented by one of the following formulae (IV) to (VI):

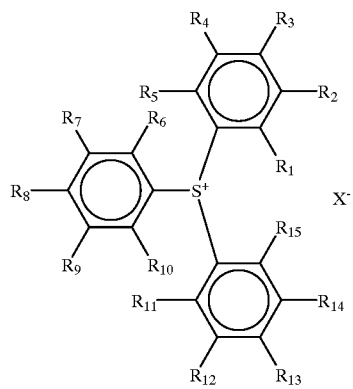
(IV)

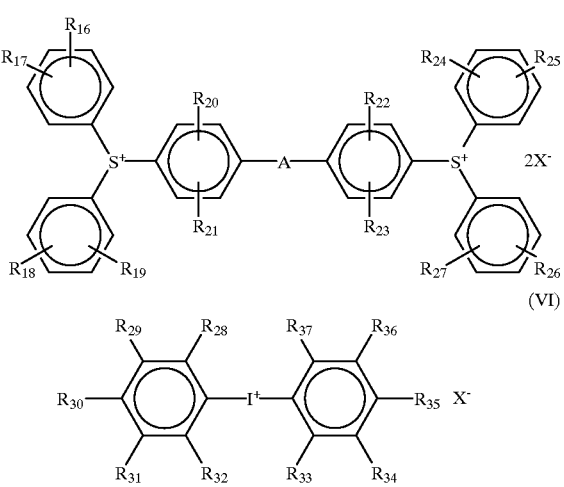
(V)

(VI)

wherein $R_1$ to $R_{37}$ each independently represents a hydrogen atom, a straight chain, branched, or cyclic alkyl group, a straight chain, branched, or cyclic alkoxy group, a hydroxy group, a halogen atom, or a —S—$R_{38}$ group (wherein $R_{38}$ represents a straight chain, branched, or cyclic alkyl group or an aryl group); X$^-$ represents an anion of the compound represented by the formula (I); A represents a single bond, a sulfur atom, an oxygen atom, or a methylene group.

(8). The positive resist composition according to the above item (7), wherein X$^-$ in the formulae (IV) to (VI) contains the following structure:

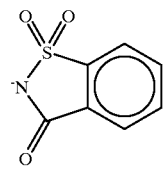

(9). The positive resist composition according to the above item (1), which further comprises (C) a compound generating sulfonic acid by irradiation with an actinic ray or a radiation.

(10). A positive resist composition comprising:

(A) a compound generating a compound represented by the formula (I) below by irradiation with an actinic ray or a radiation;

(D) a compound having a molecular weight of not larger than 3000, which is decomposed by the action of an acid to increase the solubility in an alkali developer; and (E) an alkali-soluble resin:

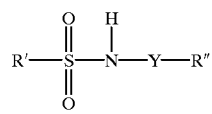
(I)

wherein, Y represents a single bond, —CO—, or —SO$_2$—; R' and R", which may be the same or different, each represents a straight chain, branched, or cyclic alkyl group which may be substituted, an aryl group which may be substituted, an aralkyl group which may be substituted, or a camphor group; R' and R" may be bonded to each other to form an alkylene group, an arylene group, or an aralkylene group, thereby, the structure of the formula (I) may form a ring; and when Y is a —CO— group, R" may be a hydroxy group or an alkoxy group.

(11). The positive resist composition according to the above item (10), wherein the pKa of the compound represented by the formula (I) is in the range of from −5 to 5.

(12). The positive resist composition according to the above item (10), which further comprises (F) a nitrogen-containing basic compound and (G) a surfactant containing at least one of the group consisting of a fluorine atom and a silicon atom.

(13). The positive resist composition according to the above item (10), wherein the compound (A) is a compound having a structure represented by one of the following formulae (IV) to (VI):

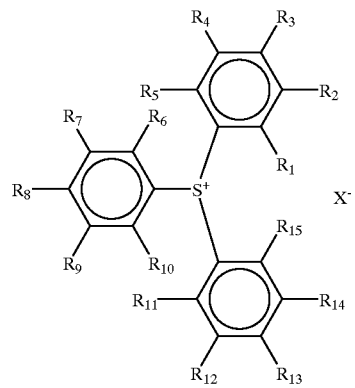
(IV)

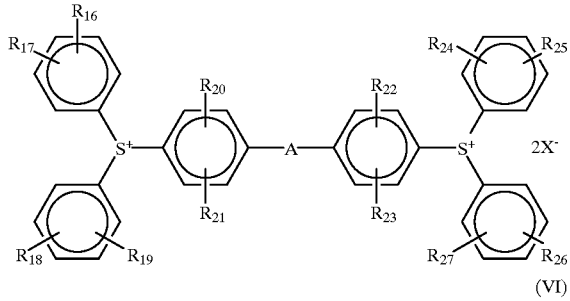
(V)

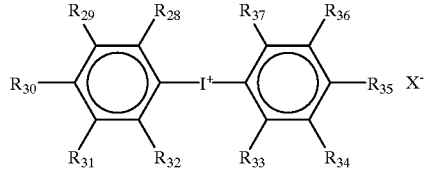
(VI)

wherein R$_1$ to R$_{37}$ each independently represents a hydrogen atom, a straight chain, branched, or cyclic alkyl group, a straight chain, branched, or cyclic alkoxy group, a hydroxy group, a halogen atom, or a —S—R$_{38}$ group (wherein R$_{38}$ represents a straight chain, branched, or cyclic alkyl group or an aryl group); X$^-$ represents an anion of the compound represented by the formula (I); A represents a single bond, a sulfur atom, an oxygen atom, or a methylene group.

(14). The positive resist composition according to the above item (13), wherein X$^-$ in the formulae (IV) to (VI) contains the following structure:

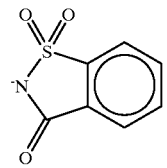

(15) The positive resist composition according to the above item (10), which further comprises (C) a compound generating sulfonic acid by irradiation with an actinic ray or a radiation.

(16). A sulfonium salt compound represented by the formula (IVa):

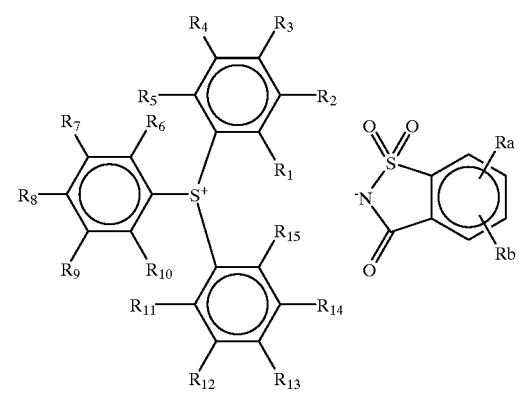
(IVa)

wherein, $R_1$ to $R_{15}$ each independently represents a hydrogen atom, a straight chain or branched alkyl group having from 1 to 5 carbon atoms, a cyclic alkyl group having from 3 to 8 carbon atoms, an alkoxy group having from 1 to 4 carbon atoms, a halogen atom, or —S—$R_{38}$ (wherein $R_{38}$ represents a straight chain or branched alkyl group having from 1 to 5 carbon atoms, a cyclic alkyl group having from 3 to 8 carbon atoms, or an aryl group having from 6 to 14 carbon atoms); Ra and Rb each independently represents a hydrogen atom, a halogen atom, an alkyl group having from 1 to 5 carbon atoms, an alkoxy group having from 1 to 5 carbon atoms, a nitro group, or a hydroxy group.

(17). The sulfonium salt compound according to the above item (16), wherein in the formula (IVa), $R_1$, $R_2$, $R_4$ to $R_7$, $R_9$ to $R_{12}$, $R_{14}$, $R_{15}$, Ra, and Rb each is a hydrogen atom, and $R_3$, $R_8$, and $R_{13}$ each independently represents a hydrogen atom, an alkyl group having from 1 to 5 atoms, an alkoxy group having from 1 to 5 carbon atoms, or a halogen atom.

(18). A sulfonium salt compound represented by the formula (Va):

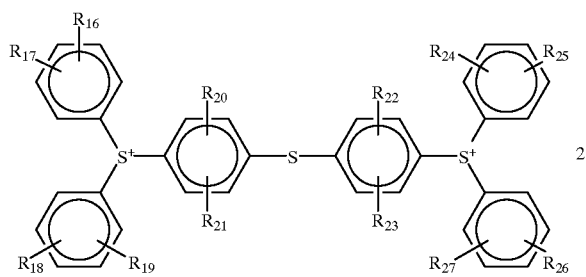

(Va)

wherein $R_{16}$ to $R_{27}$ each independently represents a hydrogen atom, a straight chain or branched alkyl group having from 1 to 5 carbon atoms, a cyclic alkyl group having from 3 to 8 carbon atoms, an alkoxy group having from 1 to 4 carbon atoms, a halogen atom, or —S—$R_{38}$ (wherein $R_{38}$ represents a straight chain or branched alkyl group having from 1 to 5 carbon atoms, a cyclic alkyl group having from 3 to 8 carbon atoms, or an aryl group having from 6 to 14 carbon atoms); Ra and Rb each independently represents a hydrogen atom, a halogen atom, an alkyl group having from 1 to 5 carbon atoms, an alkoxy group having from 1 to 5 carbon atoms, a nitro group, or a hydroxy group.

(19). The sulfonium salt compound according to the above item (18), wherein in the formula (Va), $R_{16}$ to $R_{27}$, Ra, and Rb each is a hydrogen atom.

(20). An iodonium salt compound represented by the formula (VIa):

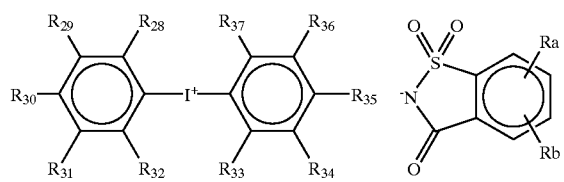

(VIa)

wherein $R_{28}$ to $R_{37}$ each independently represents a hydrogen atom, a straight chain or branched alkyl group having from 1 to 5 carbon atoms, a cyclic alkyl group having from 3 to 8 carbon atoms, an alkoxy group having from 1 to 4 carbon atoms, a halogen atom, or —S—$R_{38}$ (wherein $R_{38}$ represents a straight chain or branched alkyl group having from 1 to 5 carbon atoms, a cyclic alkyl group having from 3 to 8 carbon atoms, or an aryl group having from 6 to 14 carbon atoms); Ra and Rb each independently represents a hydrogen atom, a halogen atom, an alkyl group having from 1 to 5 carbon atoms, an alkoxy group having from 1 to 5 carbon atoms, a nitro group, or a hydroxy group.

(21). The iodonium salt compound according to the above item (20), wherein in the formula (VIa), $R_{28}$, $R_{29}$, $R_{31}$ to $R_{34}$, $R_{36}$, $R_{37}$, Ra, and Rb each is a hydrogen atom, and $R_{30}$ and $R_{35}$ each independently a hydrogen atom or an alkyl group having from 1 to 5 carbon atoms.

DETAILED DESCRIPTION OF THE INVENTION

According to the present invention, even an electron beam is used as an energy ray for exposure, the excellent performance can be obtained. In the case of irradiating a resist with an electron beam, because incident electrons have electrostatic charges and cause interaction with the atomic nuclei and electrons of substances constituting the resist, there is a problem that when electron beam strike the resist film, a scattering always occur, thereby the pattern profile is deteriorated. Also, even when the beam is irradiated by reducing the beam diameter in order to resolve fine patterns, there is a problem that the irradiated area is expanded by the scattering to deteriorate the resolving power. The composition of the invention can skillfully resolve these problems of the electron beam irradiation.

Then, the invention is described in detail.

The present invention includes;

1. the positive resist composition (hereinafter, is also referred to as "the 1st composition") comprising;
    (A) a compound generating a compound represented by the formula (I) by irradiation with an actinic ray or a radiation; and (B) a resin having a group which is decomposed by the action of an acid to increase the solubility of the composition in an alkali developer as the indispensable components, and 2. the positive resist composition (hereinafter, is also referred to as "the 2nd composition") comprising:
   (A) a compound generating a compound represented by the formula (I) by irradiation with an actinic ray or a radiation;
   (D) a compound having a molecular weight of not larger than 3000, which is decomposed by the action of an acid to increase the solubility in an alkali developer; and
   (E) an alkali-soluble resin as the indispensable components.

Hereinafter, in the case of simply describing the positive resist composition or the composition of the invention, the composition includes both the 1st composition and the 2nd composition.

At first, the components, such as the compounds, the resins, etc., which these positive resist compositions of the invention comprises are explained in detail below.

Explanation of Each Component in the Composition

[1] (A) A Compound Generating the Compound Represented by the Formula (I) by Irradiation with an Actinic Ray or a Radiation (Component (A))

In the formula (I), the straight chain, branched, or cyclic alkyl group represented by R' and R" includes a straight chain or branched alkyl group having from 1 to 20 carbon atoms, such as methyl, ethyl, propyl, isopropyl, n-butyl, sec-butyl, t-butyl, hexyl, octyl, dodecyl, etc., and a cyclic alkyl group such as cyclopropyl, cyclopentyl, cyclohexyl, etc. These alkyl groups each may have a substituent and the preferred substituent includes an alkoxy group, an acyl group, an acyloxy group, fluorine, chlorine, bromine, iodine, etc.

The aralkyl group represented by R' and R" includes an aralkyl group having from 7 to 12 carbon atoms such as benzyl, phenetyl, etc. These aralkyl may have a substituent and the preferred substituent includes an alkyl group having from 1 to 4 carbon atoms, an alkoxy group having from 1 to 4 carbon atoms, a nitro group, an acetylamino group, a halogen atom, etc.

The aryl group represented by R' and R" includes an aryl group having from 6 to 20 carbon atoms, such as phenyl, tolyl, mesityl, naphthyl, etc. These aryl groups may have a substituent and preferred substituent includes an alkyl group, an alkoxy group, an acyl group, a formyl group, a nitro group, an acylamino group, a sulfonyl amino group, a halogen atom, an aryl group, an alkoxycarbonyl group, a cyano group, etc.

The alkoxy group represented by R' and R" includes an alkoxy group having from 1 to 20 carbon atoms, such as methoxy, ethoxy, propoxy, isopropoxy, n-butoxy, isobutoxy, sec-butoxy, octyloxy, dodecyloxy, etc., and an alkoxy having a substituent, such as ethoxyethoxy, hydroxyethoxy, cyanoethoxy, etc.

R' and R" may be bonded to each other to form a ring, and practical examples of the ring formed include the rings represented by the following formulae.

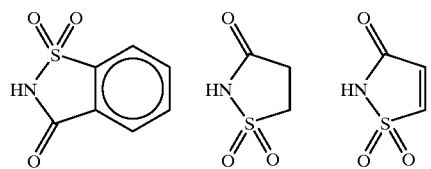

The pKa of the compounds represented by the formula (I) is preferably in the range of from −5 to 5, more preferably from −3 to 4, and particularly preferably from 0 to 5. When the pKa is smaller than −5, the acidity becomes strong and the recombination and the crosslinking reaction of the protective group decomposed by acid become liable to occur, while when the pKa is larger than 5, the decomposition of the acid-decomposable group becomes delayed, and the sensitivity becomes greatly lowered.

The pKa can be calculated by a titration using a commercially available titration apparatus or a pH meter in water or a mixed solvent of water and a water-soluble organic solvent (dioxane, methanol, tetrahydrofuran, etc.). The pKa of saccharin which is the compound represented by the above-described formula (I) is 2.3.

The positive resist composition of the invention comprises the component (A) as the indispensable component.

As the components (A), there are the sulfonium salts and the iodonium salts of the anions formed by a dissociation of N—H in the compounds represented by the formula (I). As the components (A), a compound represented by the above-described formulae (IV) to (VI) is more preferable. By using these compounds, the sensitivity, the resolving power, and the exposure margin become more excellent. By irradiating the compounds with an actinic ray or a radiation, they generate the compounds represented by the formula (I) corresponding to $X^-$ of the compounds (IV) to (VI), which function as photo-acid generator.

In the formulae (IV) to (VI), the straight chain or branched alkyl groups of $R_1$ to $R_{38}$ include the alkyl groups having from 1 to 5 carbon atoms, such as methyl, ethyl, propyl, n-butyl, sec-butyl, t-butyl, etc., each of which may have a substituent.

The cyclic alkyl group of $R_1$ to $R_{38}$ include the alkyl groups having from 3 to 8 carbon atoms, such as cyclopropyl, cyclopentyl, cyclohexyl, etc., each of which may have a substituent.

The alkoxy groups of $R_1$ to $R_{37}$ include the alkoxy groups having from 1 to 4 carbon atoms, such as methoxy, ethoxy, hydroxyethoxy, propoxy, n-butoxy, isobutoxy, sec-butoxy, t-butoxy, etc.

The halogen atoms of $R_1$ to $R_{37}$ include fluorine, chlorine, bromine, iodine, etc.

The aryl groups of $R_{38}$ include the aryl groups having from 6 to 14 carbon atoms, such as phenyl, tolyl, methoxyphenyl, naphthyl, etc., each of which may have a substituent.

The preferred substituents which can be owned by the groups of $R_1$ to $R_{38}$ include an alkyl group having from 1 to 4 carbon atoms, a halogen atom (fluorine, chlorine, iodine, etc.), an aryl group having from 6 to 10 carbon atoms, an alkenyl group having from 2 to 6 carbon atoms, a cyano group, a hydroxy group, a carboxy group, an alkoxycarbonyl group, a nitro group, etc.

X⁻ is preferably the anions represented by the following formula.

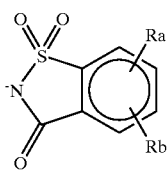

In the above formula, Ra and Rb each independently represents a hydrogen atom, a halogen atom, an alkyl group having from 1 to 5 carbon atoms, an alkoxy group having from 1 to 5 carbon atoms, a nitro group, or a hydroxy group. Ra and Rb each is preferably a hydrogen atom.

In the above-described formulae (IV) to (VI), $R_1$ to $R_{37}$ each is preferably a hydrogen atom. Furthermore, $R_3$, $R_8$, and $R_{13}$ each is also preferably an alkyl group having from 1 to 5 carbon atoms (for example, methyl, ethyl, and pentyl), an alkoxy group having from 1 to 5 carbon atoms (for example, butoxy), or a halogen atom (for example, chlorine) in addition to a hydrogen atom. $R_{30}$ and $R_{35}$ each is also preferably an alkyl group having from 1 to 5 carbon atoms (for example, methyl, butyl, and pentyl) in addition of a hydrogen atom.

In the formula (V), A is preferably a sulfur atom.

Then, practical examples of the component (A) (photo-acid generator) are shown below, but the invention is not limited by these compounds.

Practical examples (VI-1) to (IV-18) of the photo-acid generators represented by the formula (IV) described above are illustrated below.

(IV-1)

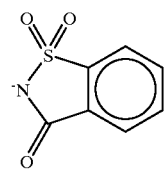

(IV-2)

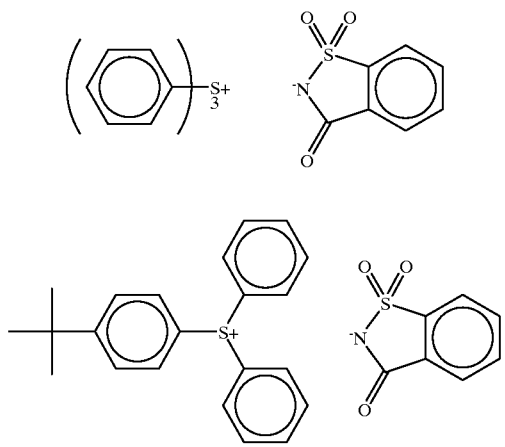

(IV-3)

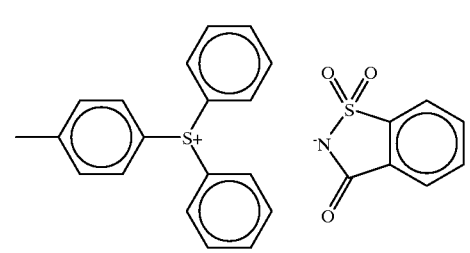

(IV-4)

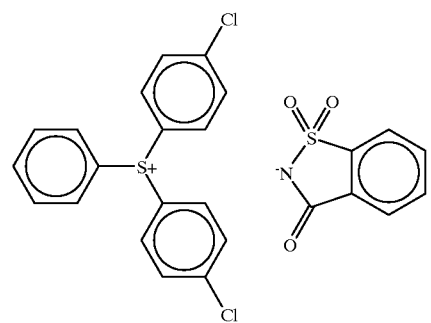

(IV-5)

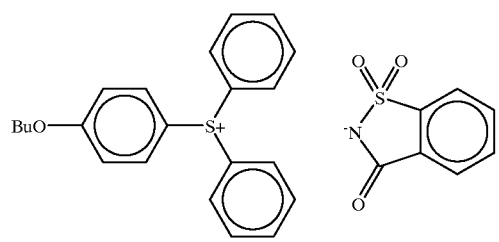

(IV-6)

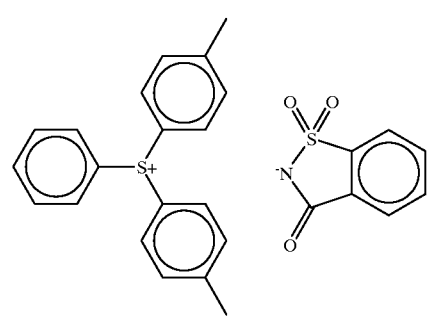

(IV-7)

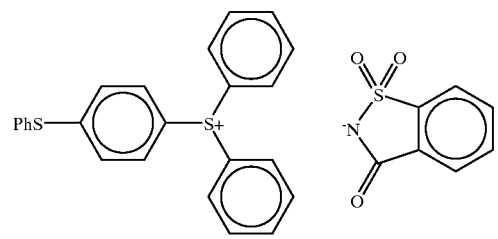

(IV-8)

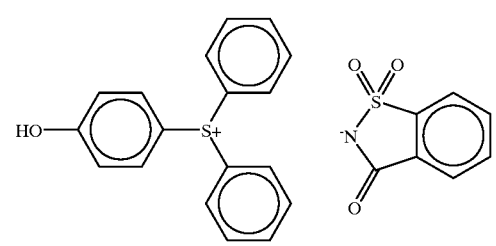

(IV-9)

-continued
(IV-10)
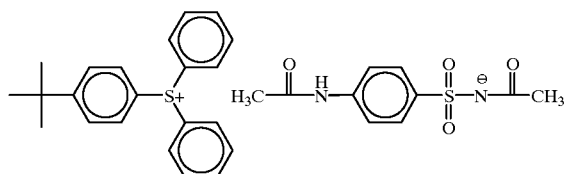
(IV-11)
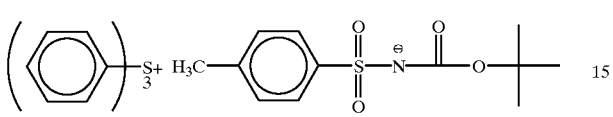
(IV-12)
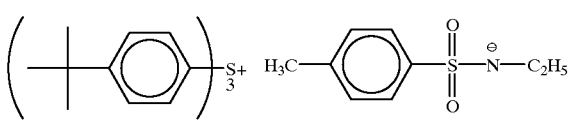
(IV-13)
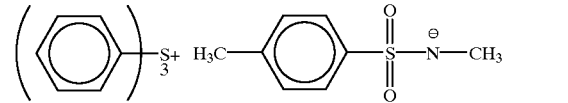
(IV-14)
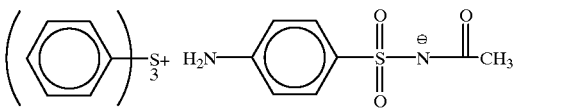
(IV-15)
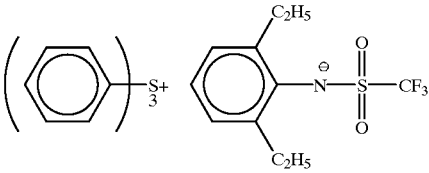
(IV-16)
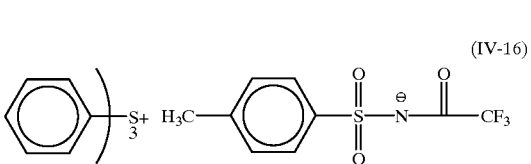
(IV-17)
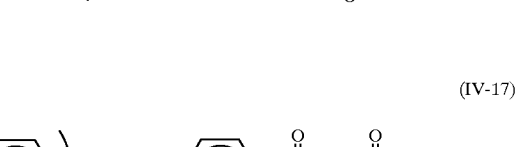
(IV-18)
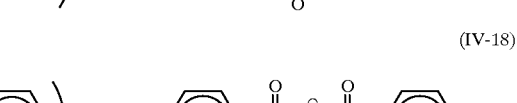
Practical examples (V-1) to (V-7) of the photo-acid generator represented by the formula (V) are shown below.
(V-1)
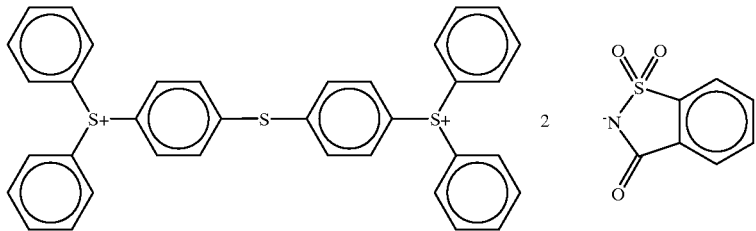
(V-2)
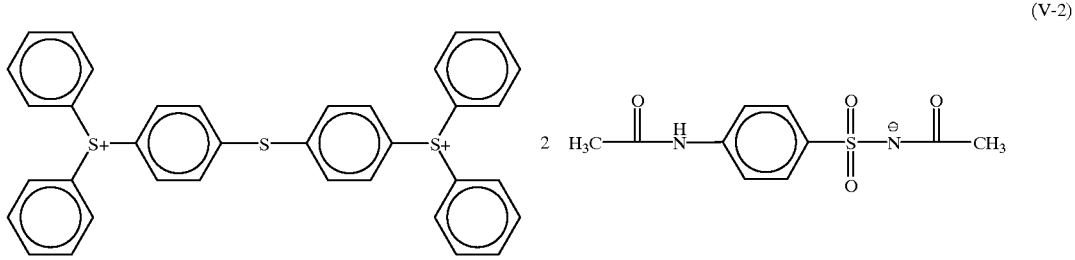

(V-3)
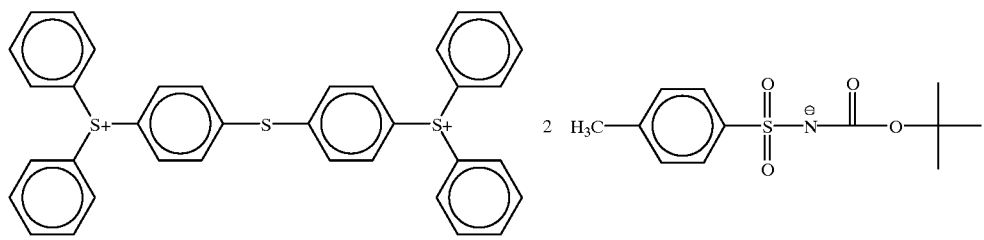
(V-4)
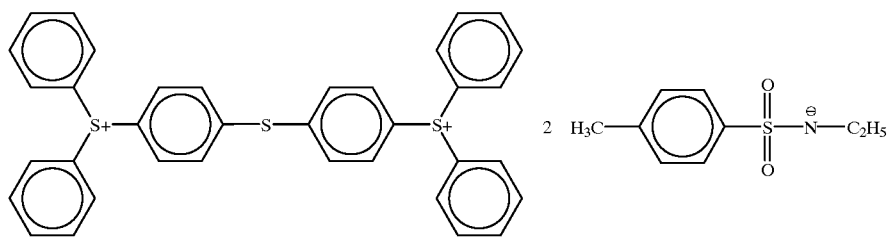
(V-5)
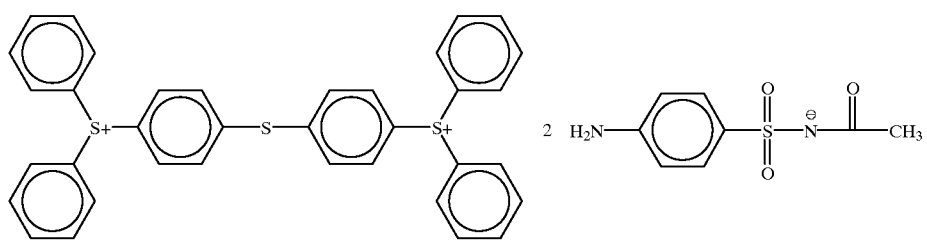
(V-6)
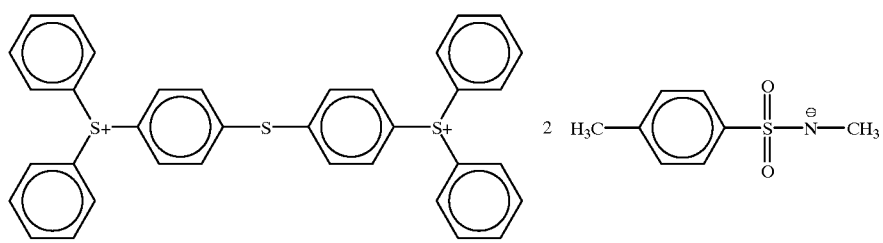
(V-7)
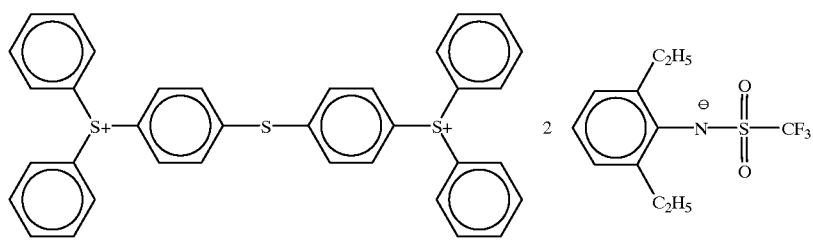
Practical examples (VI-1) to (VI-11) of the photo-acid generators represented by the formula (VI) are shown below.
-continued
(VI-1)
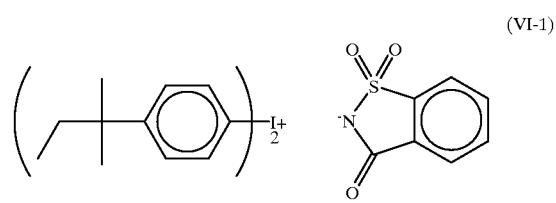
(VI-2)
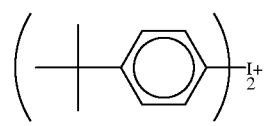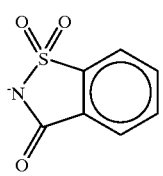

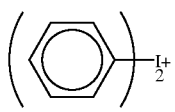 (VI-3)
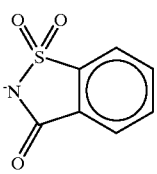

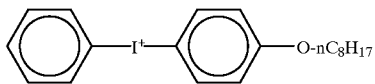 (VI-4)
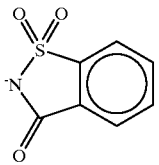

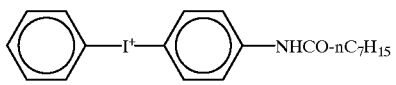 (VI-5)

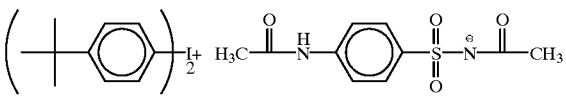 (VI-6)

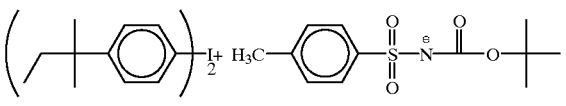 (VI-7)

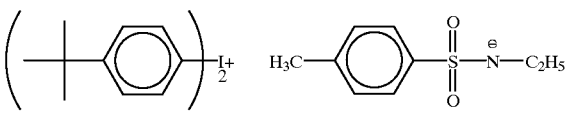 (VI-8)

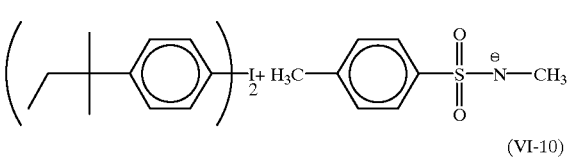 (VI-9)

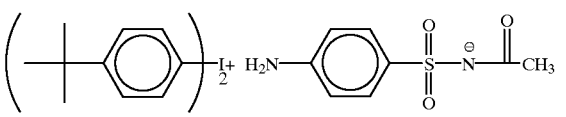 (VI-10)

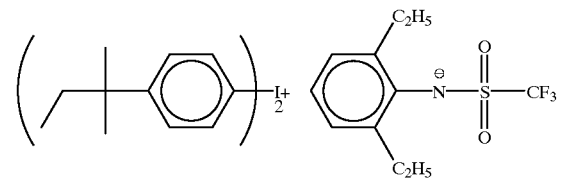 (VI-11)

The component (A) can be used singly or as a combination of two or more kinds of them.

For obtaining the compound represented by the formulae (IV) to (VI), the corresponding sulfonium or iodonium halogen compound is reacted with silver oxide to covert to the onium hydroxide, and thereafter, by adding the corresponding sulfonylimide compound, the desired compound is obtained.

The content of the compound of the component (A) in the positive resist composition of the invention is preferably from 0.1 to 20% by weight, more preferably from 0.5 to 10% by weight, and far more preferably from 1 to 7% by weight based on the solid components of the composition.

[2] Photo-acid Generator (Component (C)), which may be used Together with the Component (A)

Other photo-acid generator(component (C)) than the component (A) is used in the composition of the present invention.

As the photo-acid generator, which can be used together with the component (A), a photo-initiator for cationic photopolymerization, a photo-initiator for radical photopolymerization, a photodecolouring agent for agent, a photodiscoloring agent, a compound generating an acid by a known light used for a microresist, etc., (ultraviolet rays of from 400 to 200 nm, far ultraviolet rays, and particularly preferably g-line, h-line, I-line, a KrF excimer laser light), an ArF excimer laser light, electron beam, X-ray, a molecular beam, or an ion beam, and a mixture of them can be properly selected.

Also, other photo-acid generators, which can be used together with the component (A) include, for example, onium salts such as a diazonium salt, an ammonium salt, a phosphonium salt, an iodonium salt, a sulfonium salt, a selenonium salt, an alsonium salts, etc.; organic halogen compounds; organometal/organic halogen compounds; photo-acid generators having an o-nitrobenzyl-type protective group; compounds generating sulfonic acid by being photodecomposed, such as imino sulfonate; disulfone compounds; diazoketosulfone; and diazodisulfone compounds.

Also, the compounds each obtained by introducing the group or the compound generating an acid by light to the main chain or the side chain of the polymer can be used together with the component (A).

Furthermore, the compounds each generating an acid by light described in V. N. R. Pillai, "Synthesis", (1), 1 (1980), A Abad et al., "Tetrahedron Lett", (47), 4555(1971), D. H. R. Barton et al., "J. Chem. Soc.", (C), 329(1970), U.S. Pat. No. 3,779,778, European Patent 126,712, etc., can be also used together with the component (A).

In the above-described compounds each generating an acid by being decomposed by irradiation with an actinic ray or a radiation, the compound which are particularly effectively used are the compounds represented by the formula (PAG3), the formula (PAG4), the formula (PAG6) or the formula (PAG7) described below.

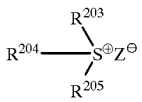 (PAG3)

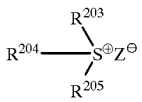 (PAG4)

-continued

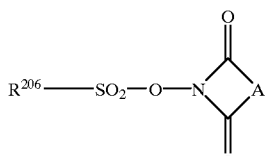
(PAG6)

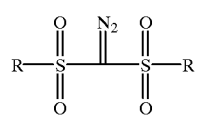
(PAG7)

In the formula (PAG3) and (PAG4), $Ar^1$ and $Ar^2$, which are the same or different, each represents substituted or unsubstituted aryl group. The preferred substituent includes an alkyl group, a haloalkyl group, a cycloalkyl group, an aryl group, an alkoxy group, a nitro group, a carboxy group, an alkoxycarbonyl group, a hydroxy group, a mercapto group, and a halogen atom.

Also, in the same formulae, $R^{203}$, $R^{204}$, and $R^{205}$, which are the same or different, each represents a substituted or unsubstituted alkyl group or a substituted or unsubstituted aryl group. Each is preferably an aryl group having from 6 to 14 carbon atoms, and alkyl group having from 1 to 8 carbon atoms, and the substituted derivatives of them. The preferred substituents for the aryl group include an alkoxy group having from 1 to 8 carbon atoms, an alkyl group having from 1 to 8 carbon atoms, a nitro group, a carboxy group, a hydroxy group and a halogen atom, and the preferred substituents for the alkyl group include an alkoxy group having from 1 to 8 carbon atoms, a carboxy group, and an alkoxycarbonyl group.

Also, $Z^-$ represents an counter anion and examples of the counter anion include $BF_4^-$, $AsF_6^-$, $PF_6^-$, $SbF_6^-$, $SiF_6^-$, $ClO_4^-$, an alkanesulfonic acid which may be substituted, a perfluoroalkanesulfonic acid, a benzenesulfonic acid which may be substituted, a naphthalenesulfonic acid which may be substituted, anthracenesulfonic acid which may be substituted, and camphorsulfonic acid which may be substituted, but $Z^-$ is not limited to them. Preferred anions are alkanesulfonic acid, perfluoroalkanesulfonic acid, an alkyl-substituted benzenesulfonic acid, and pentafluorobenzenesulfonic acid.

Also, two of $R^{203}$, $R^{204}$, and $R^{205}$ or $Ar^1$ and $Ar^2$ may be bonded to each other via a single bond or a substituent.

In the formulae (PAG6) and (PAG7), $R^{206}$ represents a substituted or unsubstituted alkyl or aryl group; A represents a substituted or unsubstituted alkylene, alkenylene, or arylene group; and R represents a straight chain, branched or cyclic alkyl group, or an aryl group which may be substituted.

As the practical examples of the compounds of the above-described formulae, there are following compounds, but the is not limited to these compounds.

(PAG3-1)
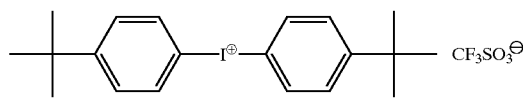

(PAG3-2)
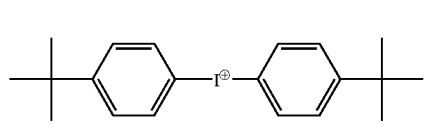

(PAG3-3)
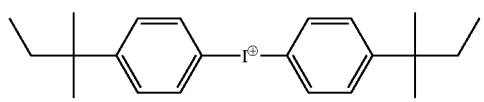
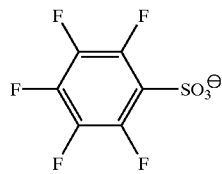

(PAG3-4)
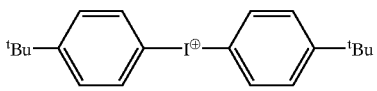

(PAG3-5)
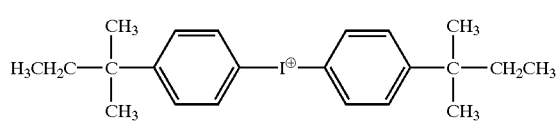
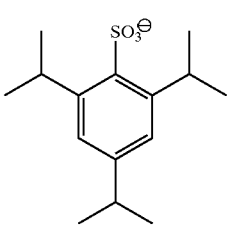

(PAG3-6)
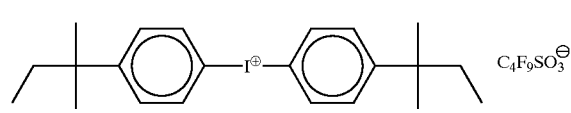

(PAG4-1)
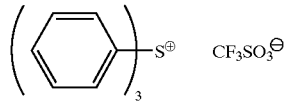

-continued
(PAG4-2) 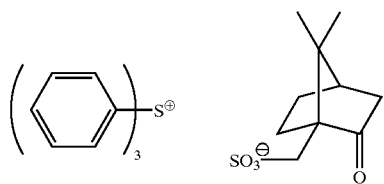
(PAG4-3) 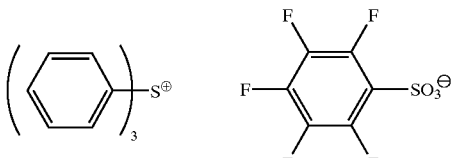
(PAG4-4) 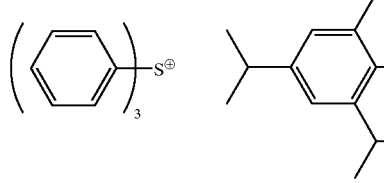
(PAG4-5) 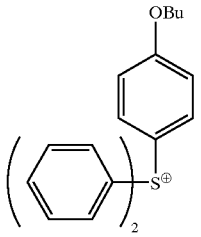
(PAG4-6) 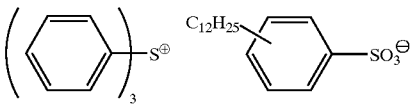
(PAG4-7) 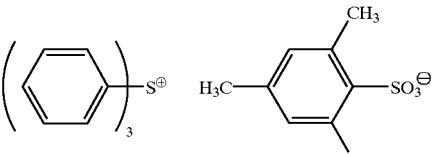
(PAG4-8) 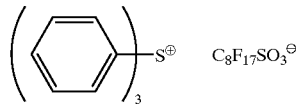
(PAG4-9) 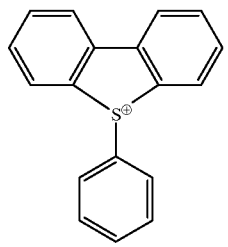
(PAG4-10) 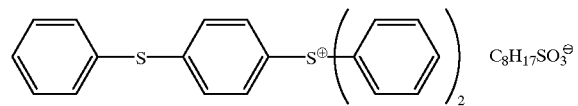
(PAG4-11) 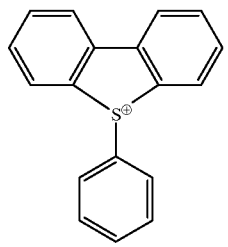
(PAG4-12) 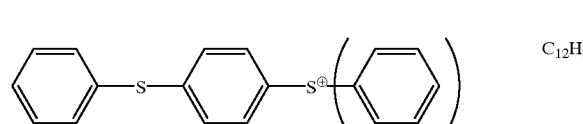
(PAG4-13) 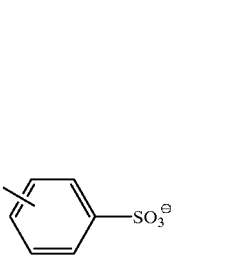
(PAG4-14) 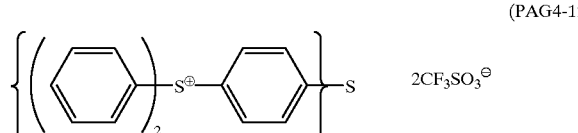
(PAG4-15) 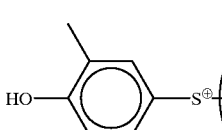

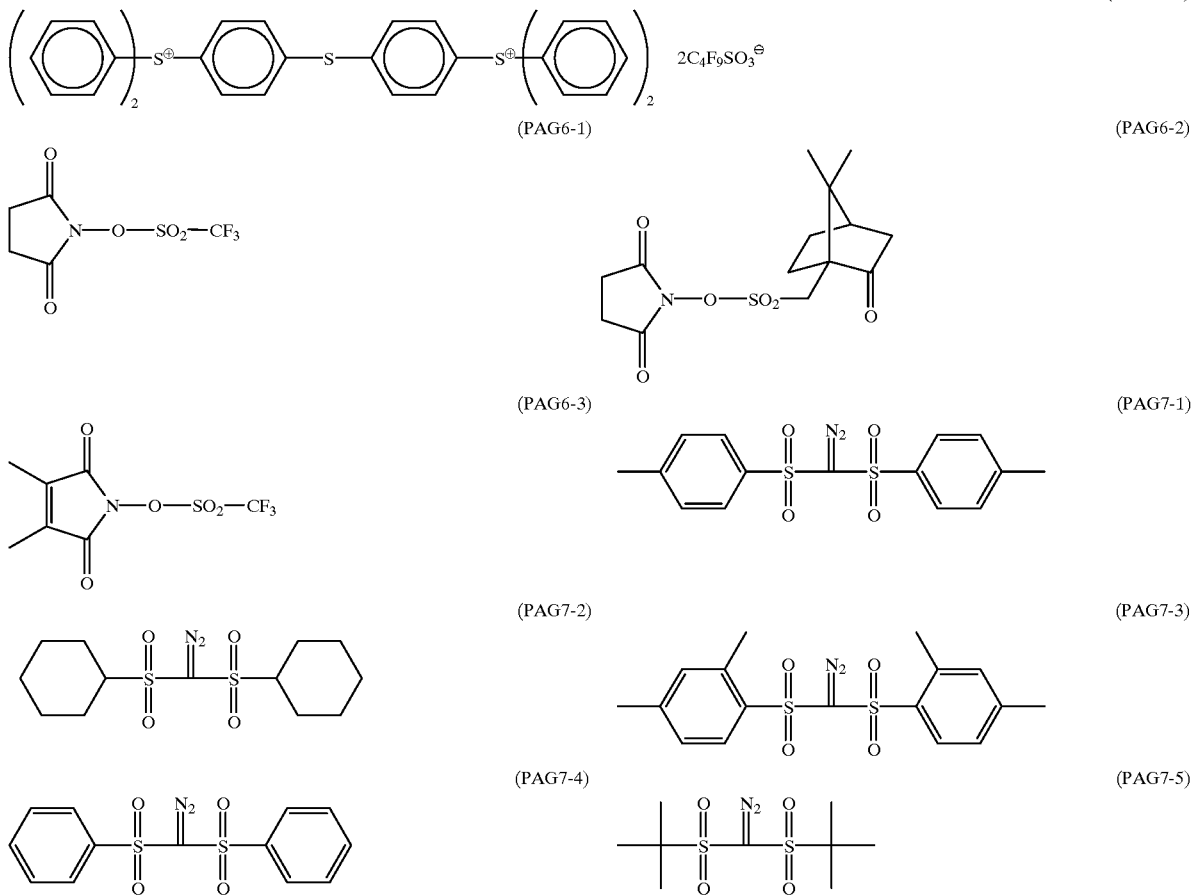

In the invention, in the above-described photo-acid generators which are used together with the component (A) described above, the compounds generating a sulfonic acid by irradiation with an actinic ray or a radiation are preferred in the point of being excellent in the sensitivity and the resolving power.

Also, in the invention, as the photo-acid generator which is used together with the component (A), the compounds represented by the formula (PAG-3), the formula (PAG-4) and the formula (PAG-7) described above are preferred.

The composition of the present invention contains the compound (C) in an amount of 5 wt % or less, preferably 4 wt % or less based on the solid contents of the composition.

[3] (B) Resin (Component (B)) Having a Group, which is Decomposed by the Action of an Acid to Increase the Solubility of the Composition in an Alkali Developer The component (B) is used as the indispensable component of the 1st component of the invention.

The component (B), that is the resin having a group, which is decomposed by an acid to increase the solubility in an alkali developer, (the group is also referred to be a group decomposable with acid), is a resin having the group decomposable with acid at the main chain or the side chain, or at both the main chain and the side chain of the resin. In these resins, the resin having the group decomposable with acid at the side chain is more preferred.

As the group decomposable with acid, the groups represented by —COOA$^0$ and —O—B$^0$ are preferable and as the group containing each of these groups, there is the group represented by —R$^0$—COOA$^0$ or —Ar—O—B$^0$.

Wherein, A$^0$ represents a group represented by —C(R$^{01}$)(R$^{02}$)(R$^{03}$), —Si(R$^{01}$)(R$^{02}$)(R$^{03}$), or —C(R$^{04}$)(R$^{05}$)—O—R$^{06}$. B$^0$ shows a group represented by A$^0$ or —CO—O—A$^0$ (R$^0$, R$^{01}$ to R$^{06}$, and Ar have the same meanings as those described below.).

The acid-decomposable group preferably includes a silyl ether group, a cumyl ester group, an acetal group, a tetrahydropyranyl ether group, an enol ether group, an enol ester group, a tertiary alkyl ether group, a tertiary alkyl ester group, a tertiary alkyl carbonate group, etc., more preferably includes a tertiary alkyl ester group, a tertiary alkyl carbonate group, a cumyl ester group, an acetal group, and a tetrahydropyranyl ether group, and particularly preferably includes an acetal group.

Then, the matrix resin in the case of bonding the group decomposable with acid to the side chain thereof is an alkali-soluble resin having —OH or —COOH, and preferably —R$^0$—COOH or —Ar—OH at the side chain. For example, where are the alkali-soluble resins described below.

The alkali-solving speed of the alkali-soluble resin is preferably at least 170 A/second by, and particularly preferably at least 330 A/second (wherein, A shows angstrom) measuring (at 23° C.) with 0.261 N of tetramethylammonium hydroxide (TMAH).

Also, from the point of attaining a rectangular profile, the alkali-soluble resin having a high transmittance to a far ultraviolet light or an excimer laser light is preferred. It is preferred that the transmittance of a film thickness of 1 μm at 248 nm is from 20 to 90%.

From such view points, the particularly preferred alkali-soluble resins include o-, m-, or p-poly(hydroxystyrene) and the copolymers of them, hydrogenated poly (hydroxystyrene), a halogen- or alkyl-substituted poly (hydroxystyrene), an o-alkylated or o-acylated product of a part of poly(hydroxystyrene), a styrene-hydroxystyrene copolymer, an α-methylstyrene-hydroxystyrene copolymer, and a hydrogenated novolac resin.

The resins having a group decomposable with acid, which are used in the invention, can be obtained by reacting the alkali-soluble resin and precursors of the group decomposable with acid, or by copolymerizing an alkali-soluble monomer bonded to the group decomposable with acid and various monomers as disclosed in European Patent 254853, Japanese Patent Laid-Open Nos. 25850/1990, 223860/1991, 251259/1992, etc.

Practical examples of the resin having the group decomposable with acid, which are used in the invention, are illustrated below but the invention is not limited to them.

p-t-butoxystyrene/p-hydroxystyrene copolymer,
p-(t-butoxycarbonyloxy)styrene/p-hydroxystyrene copolymer,
p-(t-butoxycarbonylmethyloxy)styrene/p-hydroxystyrene copolymer,
4-(t-butoxycarbonylmethyloxy)-3-methylstyrene/4-hydroxy-3-methylstyrene copolymer,
p-(t-butoxycarbonylmethyloxy) styrene/p-hydroxystyrene (10% hydrogenated product) copolymer,
m-(t-butoxycarbonylmethyloxy) styrene/m-hydroxystyrene copolymer,
o-(t-t-butoxycarbonylmethyloxy)styrene/o-hydroxystyrene copolymer,
p-(cumyloxycarbonylmethyloxy)styrene/p-hydroxystyrene copolymer,
cumyl methacrylate/methyl methacrylate copolymer,
4-t-butoxycarbonylstyrene/dimethyl maleate copolymer,
benzyl methacrylate/tetrahydropyranyl methacrylate,
p-(t-butoxycarbonylmethyloxy)styrene/p-hydroxystyrene/styrene copolymer,
p-t-butoxystyrene/p-hydroxystyrene/fumalonitrile copolymer,
t-butoxystyrene/hydroxyethyl methacrylate copolymer,
styrene/N-(4-hydroxyphenyl)maleimide/N-(4-t-butoxycarbon yloxyphenyl)maleimide copolymer,
p-hydroxystyrene/t-butyl methacrylate copolymer,
styrene/p-hydroxystyrene/t-butyl methacrylate copolymer,
p-hydroxystyrene/t-butyl acrylate copolymer,
styrene/p-hydroxystyrene/t-butyl acrylate copolymer,
p-(t-butoxycarbonylmethyloxy)styrene/p-hydroxystyrene/N-methylmaleimide copolymer,
t-butyl methacrylate/1-adamantylmethyl methacrylate copolymer,
p-hydroxystyrene/t-butylacrylate/p-acetoxystyrene copolymer,
p-hydroxystyrene/t-butylacrylate/p-(t-butoxycarbonyloxy) styrene copolymer, and
p-hydroxystyrene/t-butylacrylate/p-(t-butoxycarbonylmethyloxy)styrene copolymer.

In the invention, as the resin (component (B)) having a group decomposable with acid, resins containing the repeating units represented by the formula (II) and the formula (III) described above are preferred. By using the resin, the resist composition of the invention has a high resolution and the performance change with the passage of time from the irradiation to heating becomes less.

As the alkyl group represented by L and Z in the formula (II) described above, there are straight chain, branched, and cyclic alkyl groups having from 1 to 20 carbon atoms, such as methyl, ethyl, propyl, isopropyl, n-butyl, isobutyl, t-butyl, pentyl, cyclopentyl, hexyl, cyclohexyl, octyl, dodecyl, etc.

The alkyl group may have an substituent, and the preferred substituent includes an alkyl group, an alkoxy group, a hydroxy group, a halogen atom, a nitro group, an acyl group, an acylamino group, a sulfonylamino group, an alkylthio group, an arylthio group, an aralkylthio group, etc., and as the examples of the substituted alkyl group, there are a cyclohexylethyl group, an alkylcarbonyloxymethyl group, an alkylcarbonyloxyethyl group, an arylcarbonyloxyethyl group, an aralkylcarbonyloxyethyl group, an alkyloxymethyl group, an aryloxymethyl group, an aralkyloxymethyl group, an alkyloxyethyl group, an aryloxyethyl group, an aralkyloxyethyl group, an alkylthiomethyl group, an arylthiomethyl group, an aralkylthiomethyl group, an alkylthioethyl group, an arylthioethyl group, and an aralkylthioethyl group. There is no particular restriction on the alkyl group in this case, and the alkyl group may be a chain form, a cyclic form or a branched form. For example, there are groups such as a cyclohexylcarbonyloxyethyl group, a t-butylcyclohexylcarbonyloxyethyl group, an n-butylcyclohexylcarbonyloxyethyl group, etc. Also, there is no particular restriction on the aryl group in the above-described case, there are a phenyloxyethyl group, etc., and the group may be further substituted, such as a cyclohexylphenyloxyethyl group, etc. There is also no restriction on the aralkyl group in the case, and there are, for example, a benzylcarbonyloxyethyl group, etc.

The aralkyl groups represented by L and Z of the formula (II) include the aralkyl groups having from 7 to 15 carbon atoms, such as a substituted or unsubstituted benzyl group, a substituted or unsubstituted phenetyl group. The preferred substituents of the aralkyl group include an alkoxy group, a hydroxy group, a halogen atom, a nitro group, an acyl group, an acylamino group, a sulfonylamino group, an alkylthio group, an arylthio group, an aralkylthio group, etc., and for example, there are an alkoxybenzyl group, a hydroxybenzyl group, a phenylthiophenetyl group, etc.

It is preferred that the above-described Z is a substituted alkyl group or a substituted aralkyl group in the point that the improvement of the edge roughness is further obtained. As the substituent of the alkyl group, a cyclic alkyl group, an aryloxy group, an alkylcarboxy group, an arylcarboxy group, and an aralkylcarboxy group are preferred. Also, as the substituent of the aralkyl group, an alkyl group, a cyclic alkyl group, and a hydroxy group are preferred.

The L and Z may be bonded to each other to form a 5- or 6-membered ring as described above, and as the 5- or 6-membered ring, there are a tetrahydropyran ring, a tetrahydrofuran ring, etc.

The mol ratio of repeating structural unit represented by the formula (II) and the repeating structural unit represented by the formula (III) in the above-described resin is preferably from 1/99 to 60/40, more preferably from 5/95 to 50/50, and far more preferably from 10/90 to 40/60.

The resin containing the repeating structural units represented by the formula (II) and the formula (III) may further contains a structural unit induced from other monomer.

The other monomer can include hydrogenated hydroxystyrene; a halogen-, alkoxy-, or alkyl-substituted hydroxystyrene; styrene; a halogen-, alkoxy-, acyloxy-, or alkyl-substituted styrene; maleic anhydride; acrylic acid derivatives; methacrylic acid derivatives; N-substituted maleimide, etc., but the monomer is not limited to them.

The ratio of the structural units represented by the formula (II) and the formula (III) and the structural unit of other monomer, [(II)+(III)]/[other monomer component] is from 100/0 to 50/50, preferably from 100/0 to 60/40, and more preferably from 100/0 to 70/30 by mol ratio.

Practical examples of the resin containing the repeating structural units represented by the formula (II) and the formula (III) described above and other resins which can be used in the invention are illustrated below.

(A-1) 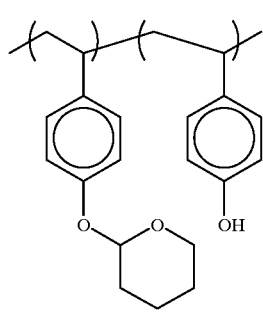
(A-2) 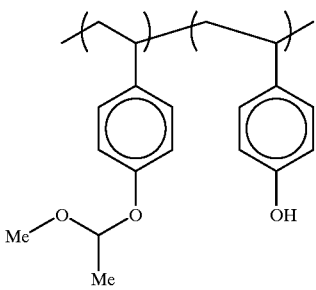
(A-3) 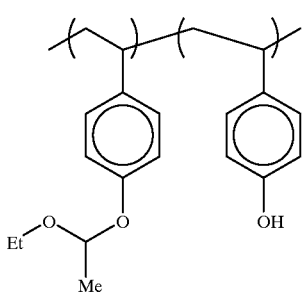
(A-4) 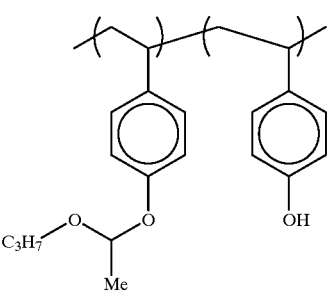
(A-5) 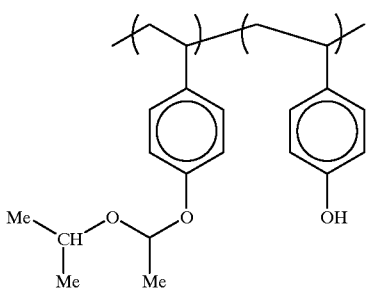
(A-6) 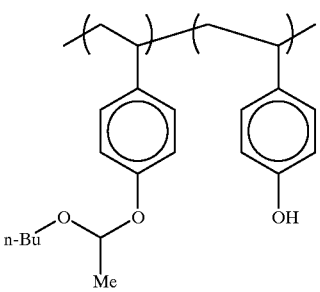
(A-7) 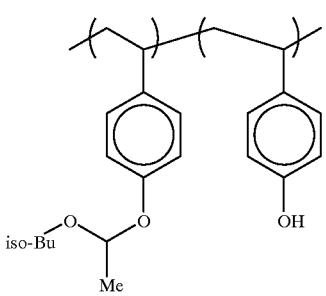
(A-8) 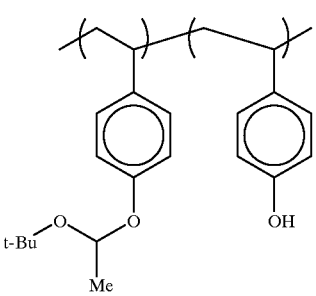
(A-9) 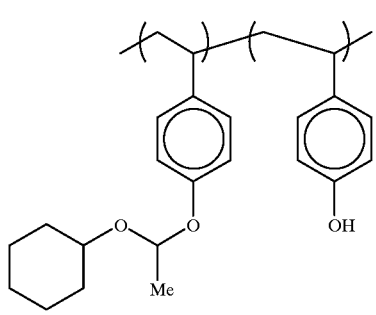
(A-10) 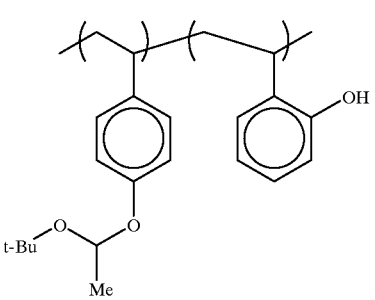

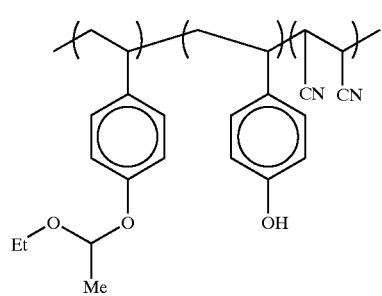
(A-11)
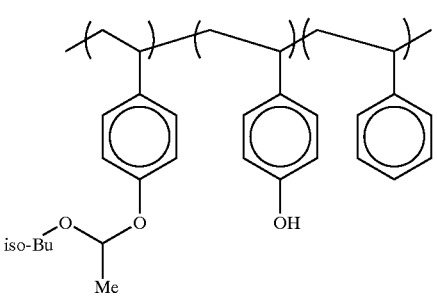
(A-12)
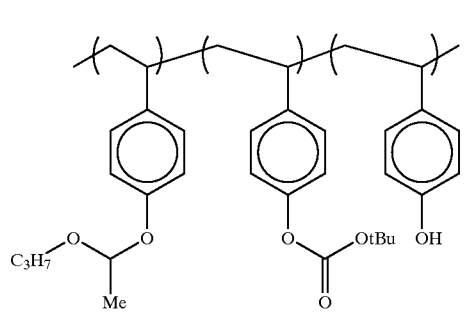
(A-13)
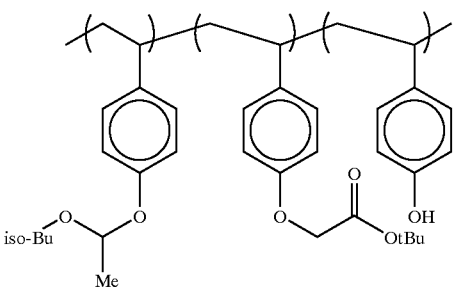
(A-14)
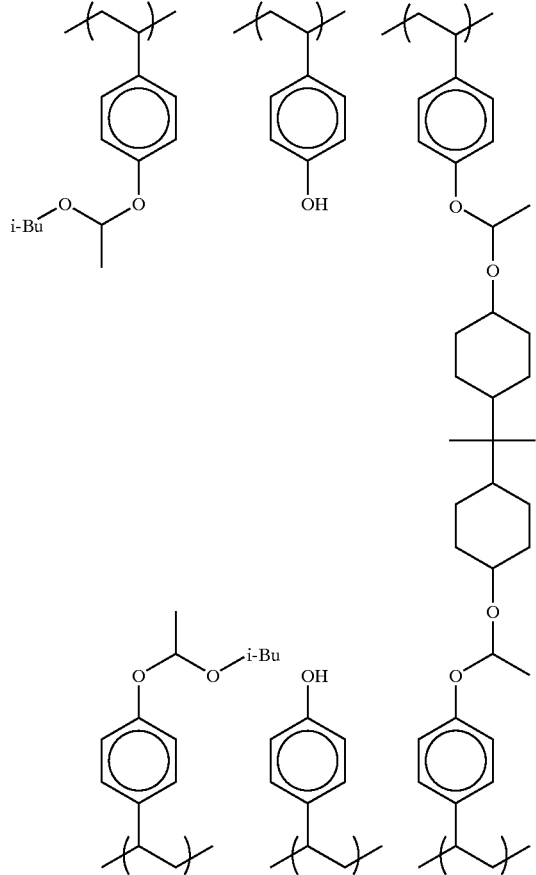
(A-15)
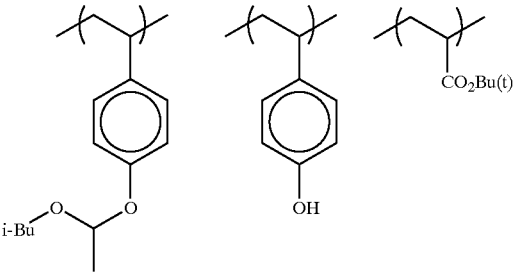
(A-16)

-continued
(A-17)
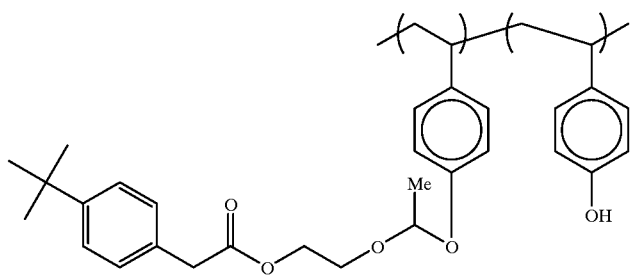
(A-18)
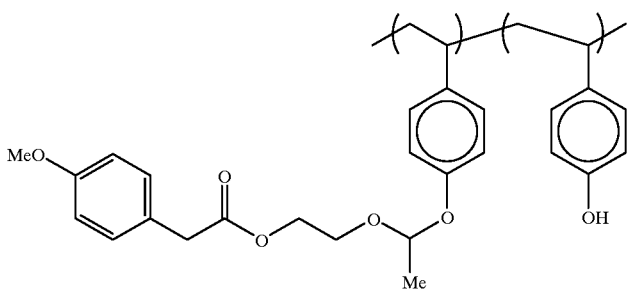
(A-19)
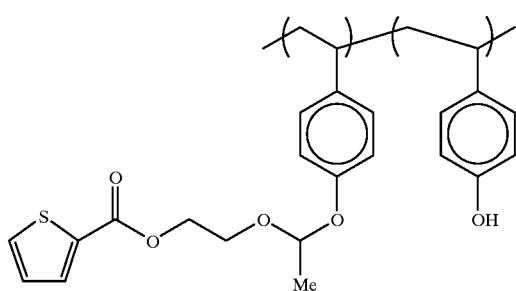
(A-20)
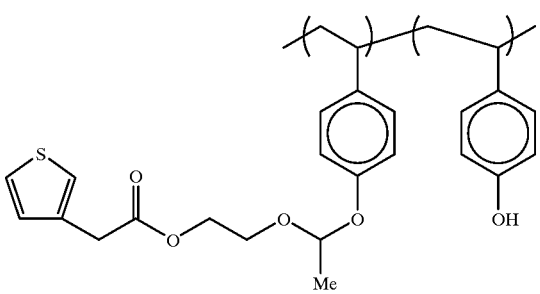
(A-21)
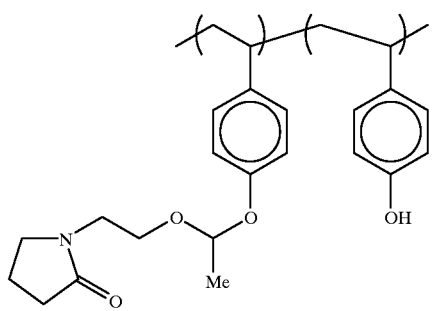
(A-22)
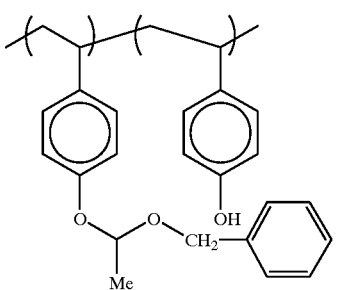
(A-23)
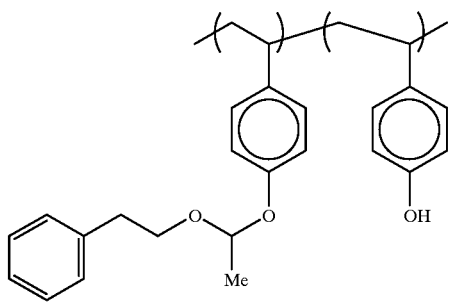
(A-24)
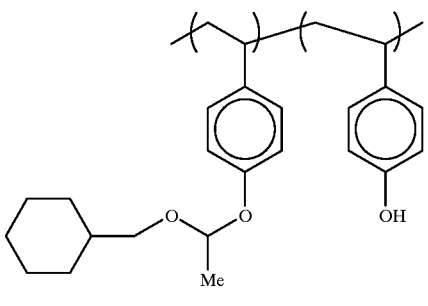

-continued
(A-25)
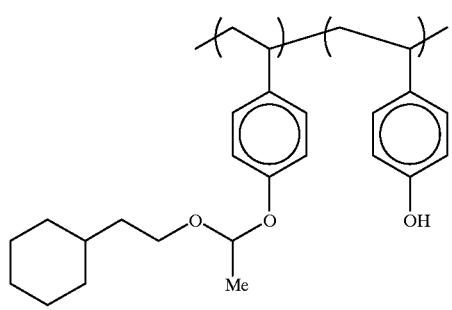
(A-26)
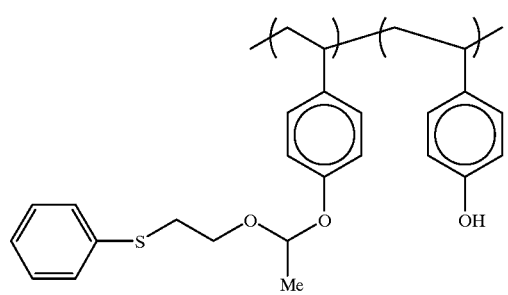
(A-27)
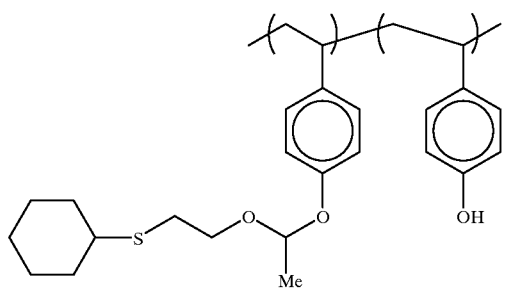
(A-28)
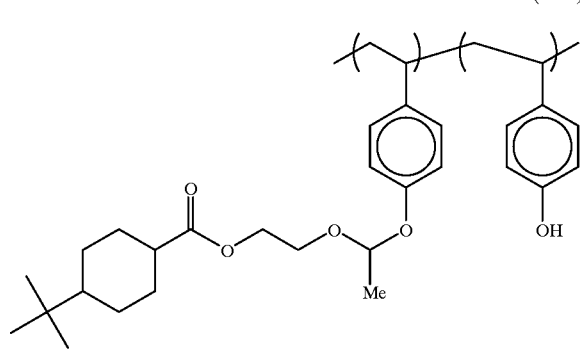
(A-29)
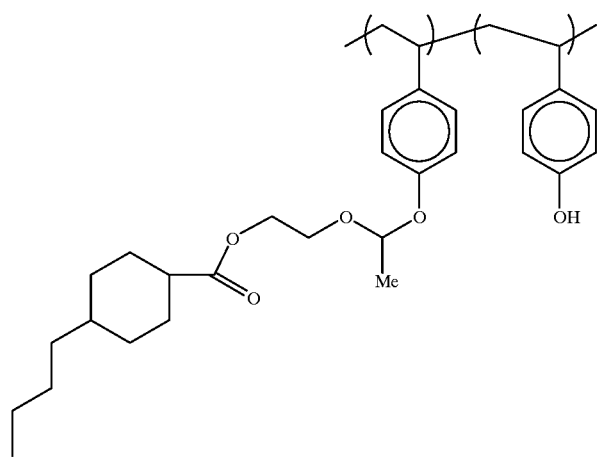
(A-30)
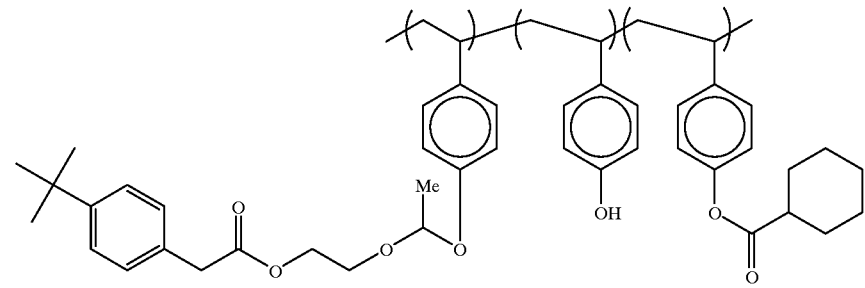

-continued
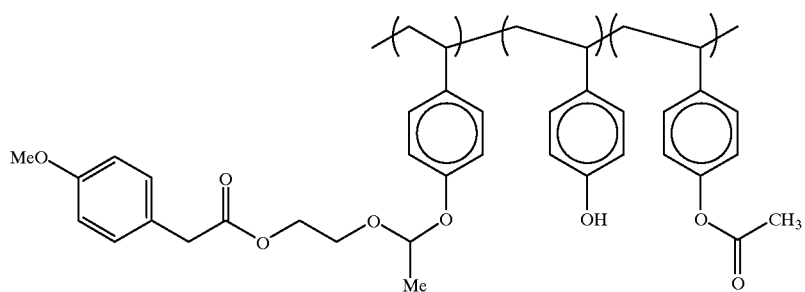
(A-31)
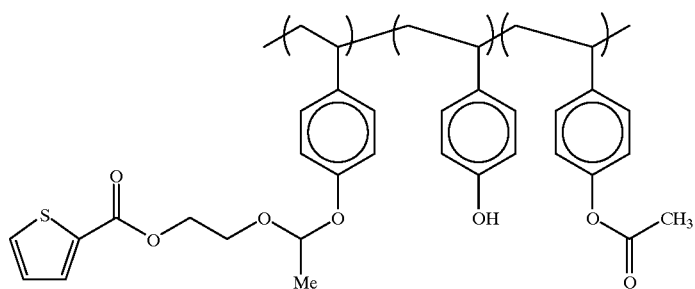
(A-32)
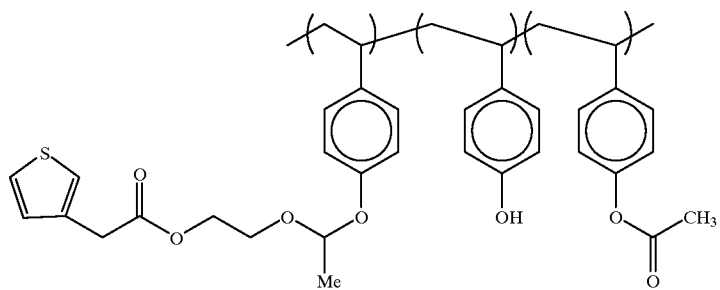
(A-33)
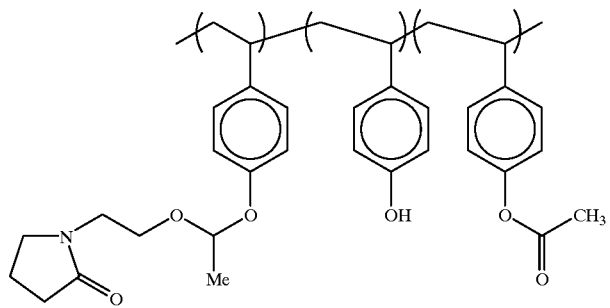
(A-34)
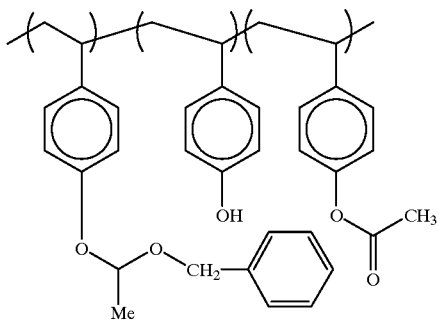
(A-35)                                      (A-36)

(A-37)
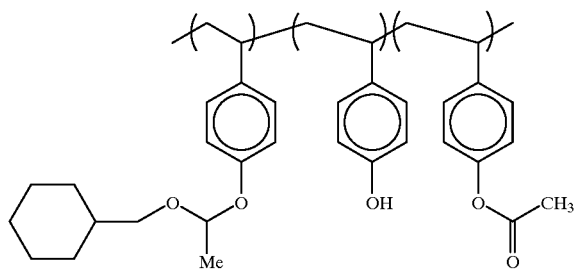
(A-38)
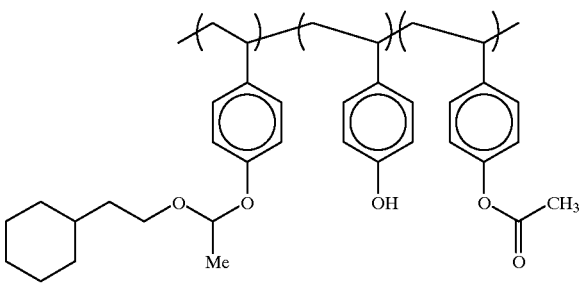
(A-39)
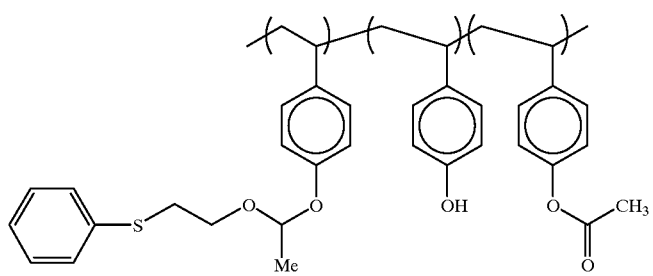
(A-40)
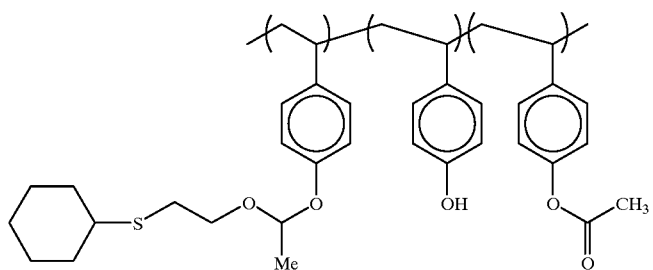
(A-41)
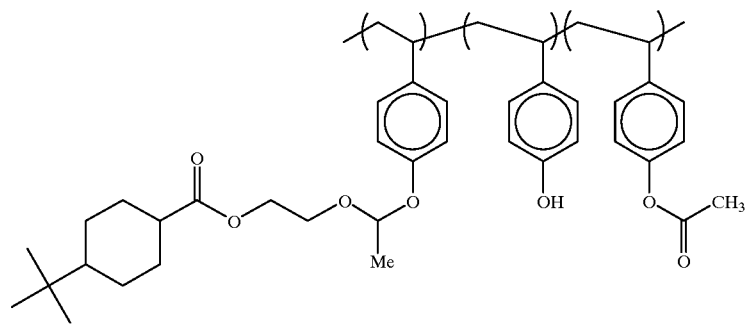

-continued
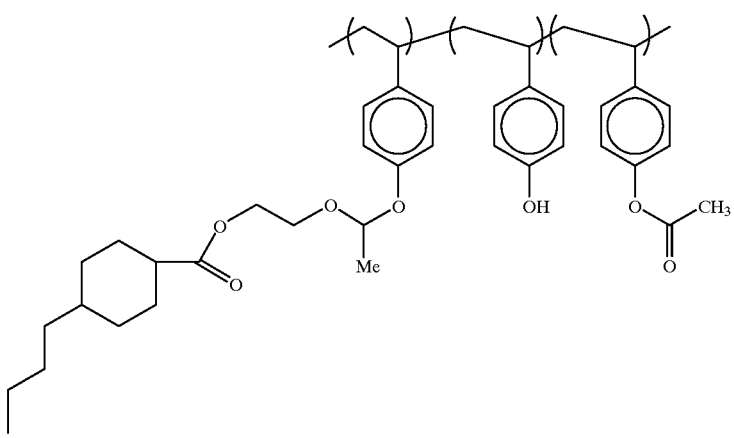
(A-42)
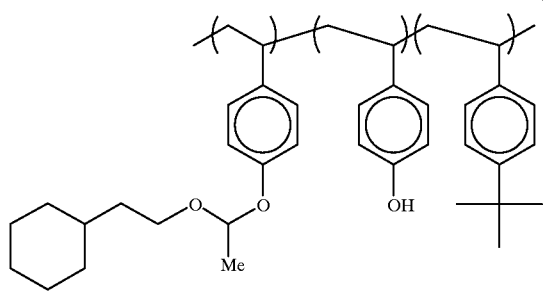
(A-43)
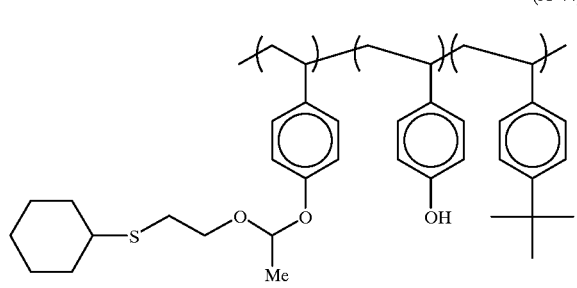
(A-44)
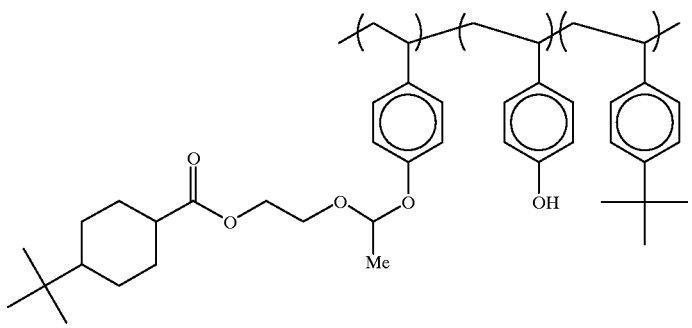
(A-45)
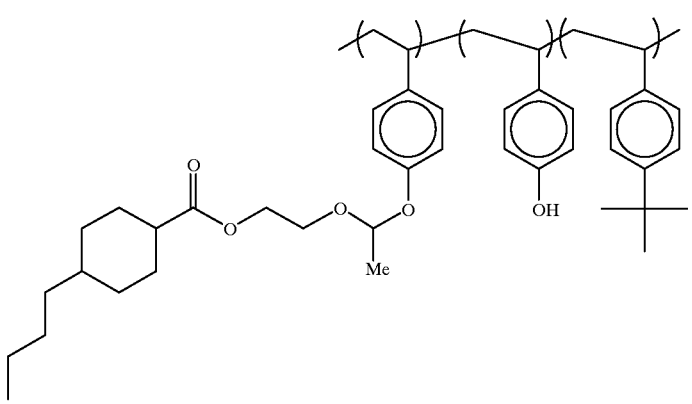
(A-46)

-continued

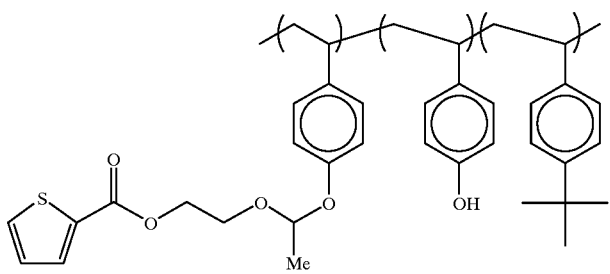
(A-47)

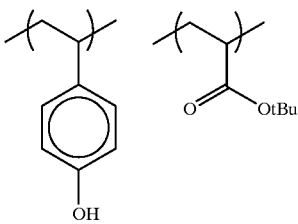
(A-48)

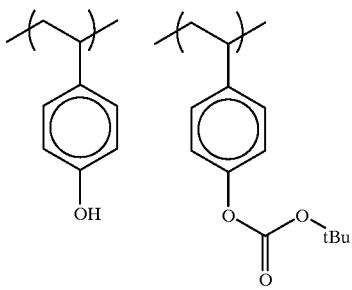
(A-49)

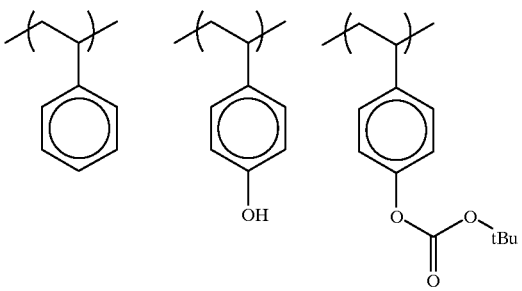
(A-50)

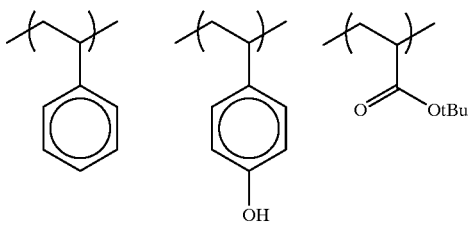
(A-51)

In the above-described practical examples, Me represents a methyl group, Et represents an ethyl group, nBu represents an n-butyl group, iso-Bu represents an isobutyl group, and tBu represents a t-butyl group.

In the case of using an acetal group as the acid-decomposable group, for controlling the alkali-solving speed and improving the heat resistance, a crosslinking site of connecting a polyfunctional acetal group to the main chain of the polymer may be introduced by adding a polyhydroxy compound in the synthesis step,. The addition amount of the polyhydroxy compound is from 0.01 to 5 mol %, and more preferably from 0.05 to 4 mol % to the amount of the hydroxy groups of the resin. The polyhydroxy compound includes a polyhydroxy compound having from 2 to 6 phenolic hydroxy groups or alcoholic hydroxy groups, preferably a polyhydroxy compound having from 2 to 4 hydroxy groups, and more preferably a polyhydroxy compound having 2 or 3 hydroxy groups.

Then, practical examples of the polyhydroxy compound are shown below, but the invention is not limited to them.

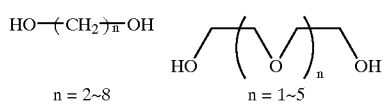

n = 2~8     n = 1~5

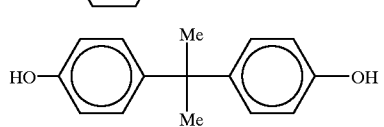

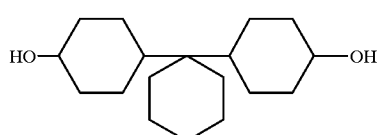

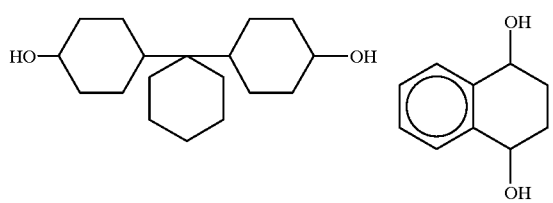

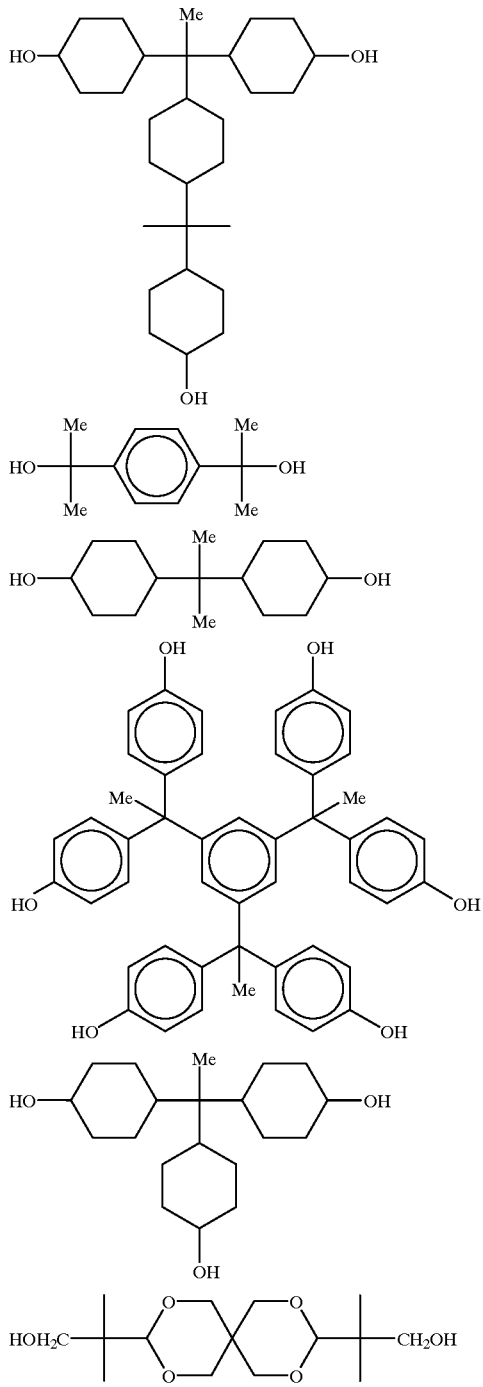

-continued

The weight average molecular weight (Mw) of the resin (B) having a group decomposable with acid is in the range of preferably from 2,000 to 300,000. When the molecular weight is less than 2,000, by the development of the non-irradiated portions of the resist film, the decrease of the resist film at the portions is large, while the molecular weight exceeds 300,000, the dissolving speed of the resin itself in alkali is delayed and the sensitivity is lowered. In this case, the weight average molecular weight is defined by the polystyrene converted value of a gel permeation chromatography.

Also, the component (B) of the positive resist composition of the invention, that is, the resin having the group decomposable by acid may be used as a mixture of two or more kinds of them.

The using amount of the component (B) is from 40 to 99% by weight, and preferably from 60 to 98% by weight based on the solid components of the 1st composition of the invention.

[4] (D) The Compound having a Molecular Weight of not Larger than 3000, which is Decomposed by the Action of an Acid to Increase the Solubility in an Alkali Developer (Component (D))

The component (D) is a component contained in the 2nd composition of the invention as the indispensable component and the component (D) is, if necessary, compounded with the 1st composition of the invention. The composition (D) is a low-molecular weight compound having a molecular weight of not larger than 3000, preferably from 200 to 2,000, and more preferably from 300 to 1,500, which has a group decomposable with acid and increases the solubility in an alkali developer by the action of acid. The component (D) has a function as a dissolution inhibitor of the non-irradiated portions to an alkali developer. In addition, the term "acid-decomposable dissolution-inhibiting compound" in the descriptions below has the same meaning as the component (D).

The preferred component (D), that is, the preferred acid-decomposable dissolution-inhibiting compound is a compound having at least two groups decomposable with acid in the structure, and the distance between the acid-decomposable groups is via at least 8 bonding atoms excluding the acid-decomposable groups in the most apart positions.

The more preferred acid-decomposable dissolution-inhibiting compounds are;

(a) a compound having at least two groups decomposable with acid in the structure, wherein the distance between the acid-decomposable groups is via at least 10, preferably at least 11, and more preferably 12 bonding atoms excluding the acid-decomposable groups in the most apart positions, and (b) a compound having at least three acid-decomposable groups, and the distance between the acid-decomposable groups is via at least 9, preferably at least 10, and more preferably 11 bonding atoms excluding the acid-decomposable groups in the most apart positions.

Also, the upper limit of the number of the above-described bonding atoms is preferably 50, and more preferably 30.

In the case where the acid-decomposable dissolution-inhibiting compound has at least 3, and preferably at least 4 acid-decomposable groups, or even in the case where the acid-decomposable dissolution-inhibiting compound has 2 acid-decomposable groups, when the acid-decomposable groups are separated from each other at a definite distance or more, the dissolution inhibiting property to the alkali-soluble resin is greatly improved.

In addition, the distance between the acid-decomposable groups is shown by the number of the bonding atoms (excluding the acid-decomposable groups) existing between the acid-decomposable groups. For example, in the cases of the compounds (1) and (2) shown below, each distance between the acid-decomposable groups is 4 bonding (carbon) atoms and in the case of compound (3) shown below, the distance between the acid-decomposable groups is 12 bonding (carbon) atoms.

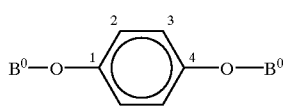

(1)

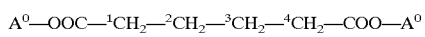

(2)

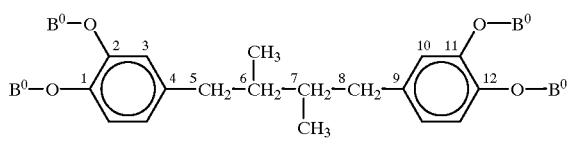

(3)

Acid-decomposable groups: —COO—A°, —O—B°

Also, the acid-decomposable dissolution-inhibiting compound may have plural acid-decomposable groups on one benzene ring but is preferably a compound comprising a skeleton having one acid-decomposable group on one benzene ring.

As the group decomposable with acid, that is, the group containing —COO—A° or —O—B°, there is a group represented by —R°—COO—A° or —Ar—O—B°.

Wherein, A° represents a group represented by —C($R^{O1}$)($R^{O2}$)($R^{O3}$), —Si($R^{O1}$)($R^{O2}$)($R^{O3}$), or —C($R^{O4}$)($R^{O5}$)—O—$R^{O6}$, and B° represents a group represented A° or —CO—O—A°.

$R^{O1}$, $R^{O2}$, $R^{O3}$, $R^{O4}$, and $R^{O5}$, which are the same or different, each represents a hydrogen atom, an alkyl group, a cycloalkyl group, an alkenyl group, or an aryl group, and $R^{O6}$ represents an alkyl group or an aryl group. Wherein, however, at least two of $R^{O1}$, $R^{O2}$, and $R^{O3}$ are groups other than a hydrogen atom; two groups of $R^{O1}$, $R^{O2}$, and $R^{O3}$ or $R^{O4}$, $R^{O5}$, and $R^{O6}$ may be bonded to each other to form a ring. Furthermore, R° represents a two valent or more aliphatic or aromatic hydrocarbon group, which may have a substituent, and —Ar— represents a two valent or more aromatic group, which may be monocyclic or polycyclic, which may have a substituent.

Wherein, the alkyl group is preferably an alkyl group having from 1 to 4 carbon atoms, such as methyl, ethyl, propyl, n-butyl, sec-butyl, t-butyl, etc.; the cycloalkyl group is preferably a cycloalkyl group having from 3 to 10 carbon atoms, such as cyclopropyl, cyclobutyl, cyclohexyl, adamantyl, etc.; the alkenyl group is preferably an alkenyl group having from 2 to 4 carbon atoms, such as vinyl, propenyl, allyl, butenyl, etc.; and the aryl group is preferably an aryl group having from 6 to 14 carbon atoms, such as phenyl, xylyl, toluyl, cumenyl, naphthyl, anthracenyl, etc.

Also, the above-described substituents include a hydroxy group, halogen atoms such as fluorine, chlorine, bromine, iodine, etc.; a nitro group, a cyano group, the alkyl groups described above; alkoxy groups such as methoxy, ethoxy, hydroxyethoxy, propoxy, hydroxypropoxy, n-butoxy, iso-butoxy, sec-butoxy, t-butoxy, etc.; alkoxycarbonyl groups such as methoxycarbonyl, ethoxycarbonyl, etc.; aralkyl groups such as benzyl, phenetyl, cumyl, etc.; an aralkyloxy group; acyl groups such as formyl, acetyl, butyryl, benzoyl, cyanamyl, valeryl, etc.; acyloxy groups such as butyryloxy, etc.; the alkenyl group described above; alkenyloxy groups such as vinyloxy, propenyloxy, allyloxy, butenyloxy, etc.; the aryl groups described above; aryloxy groups such as phenoxy, etc.; aryloxycarbonyl groups such as benzoyloxy, etc.

The acid-decomposable groups preferably include a silyl ether group, a cumyl ester group, an acetal group, a tetrahydropyranyl ether group, an enol ether group, an enol ester group, a tertiary alkyl ether group, a tertiary alkyl ester group, a tertiary alkyl carbonate group, etc., and more preferably include a tertiary alkyl ester group, a tertiary alkyl carbonate group, a cumyl ester group, and a tetrahydropyranyl ether group.

The component (D) preferably includes the compounds obtained by bonding and protecting with the above-described group, —R°—COO—A° or B° the whole or a part of the phenolic OH groups of the polyhydroxy compounds described in Japanese Patent Laid-Open Nos. 289946/1989, 289947/1989, 2560/1990, 128959/1991, 158855/1991, 179353/1991, 191351/1991, 200251/1991, 200252/1991, 200253/1991, 200254/1991, 200255/1991, 259149/1991, 279958/1991, 279959/1991, 1650/1992, 1651/1992, 11260/1992, 12356/1992, and 12357/1992, Japanese Patent Application Nos. 33229/1991, 230790/1991, 320438/1991, 25157/1992, 52732/1992, 103215/1992, 104542/1992, 107885/1992, 107889/1992, 152195/1992, etc.

More preferably, the component (D) includes the compounds obtained using the polyhydroxy compounds described in Japanese Patent Laid-Open Nos. 289946/1989, 128959/1991, 158855/1991, 179353/1991, 200251/1991, 200252/1991, 200255/1991, 259149/1991, 279958/1991, 1650/1992, 11260/1992, 12356/1992, and 12357/1992, Japanese Patent Application Nos. 25157/1992, 103215/1992, 104542/1992, 107885/1992, 107889/1992, and 152195/1992.

Practical examples of the skeletons of the preferred compounds of the components (D) in the invention are shown below.

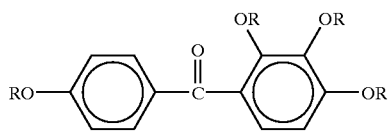

(1)

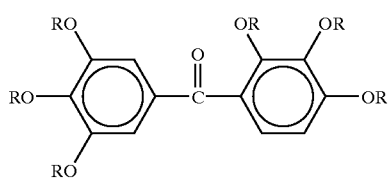

(2)

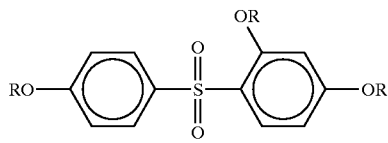

(3)

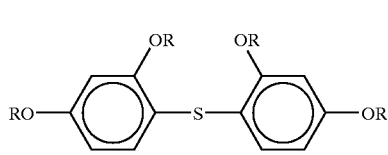

(4)

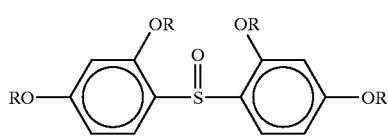

(5)

(6)
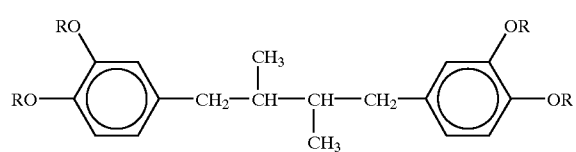
(7)
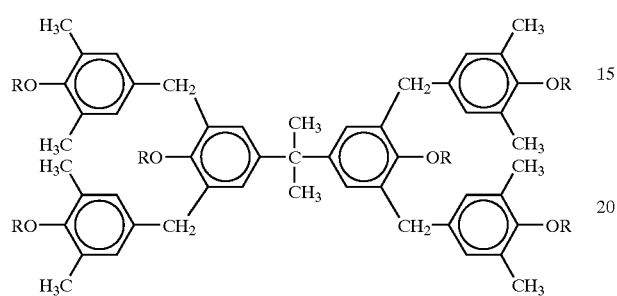
(8)
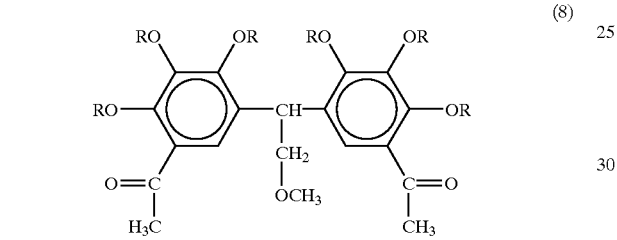
(9)
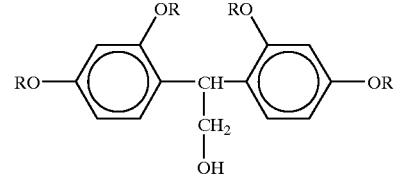
(10)
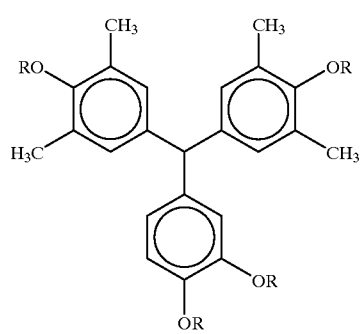
(11)
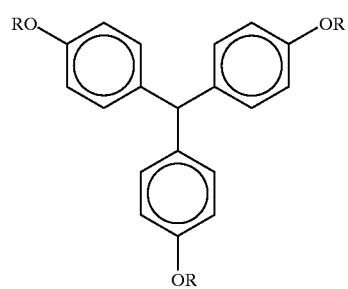
(12)
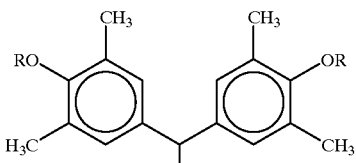
(13)
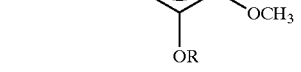
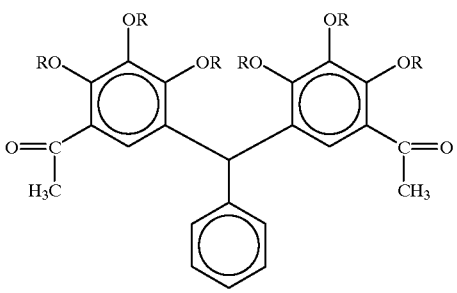
(14)
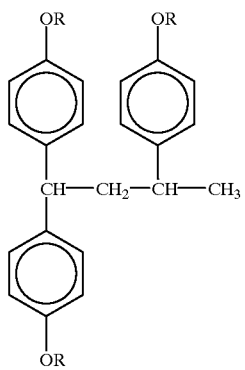
(15)
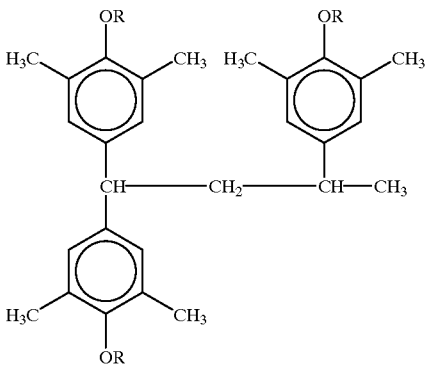

(16)
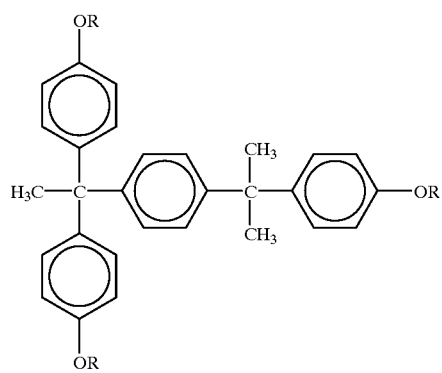
(20)
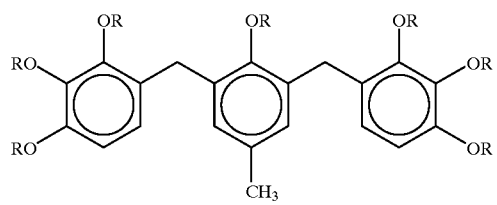
(21)
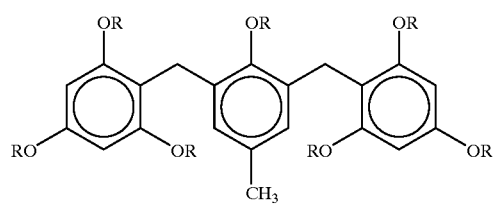
(17)
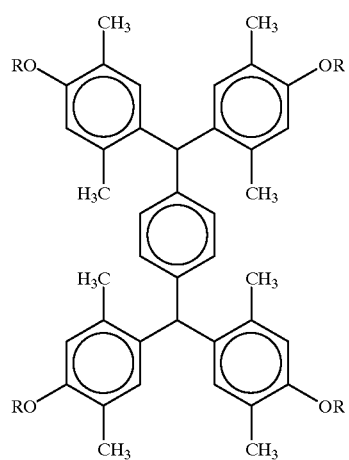
(22)
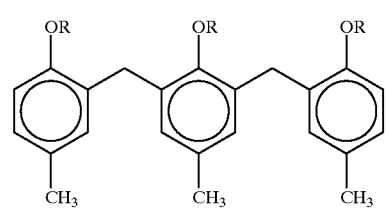
(23)
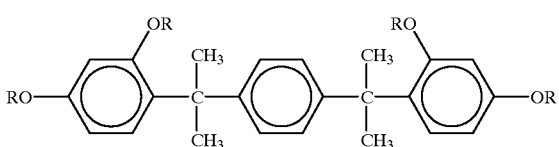
(24)
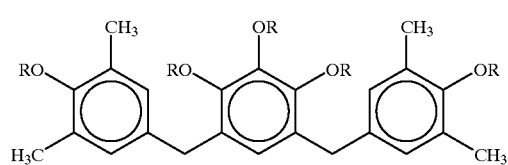
(18)
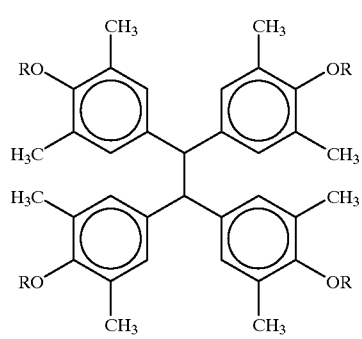
(25)
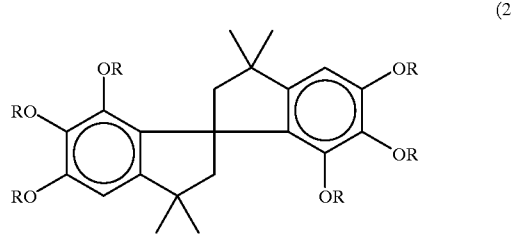
(19)
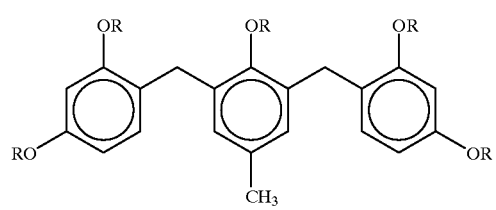
(26)
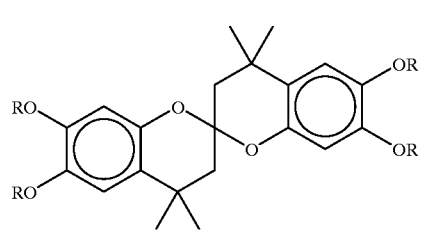

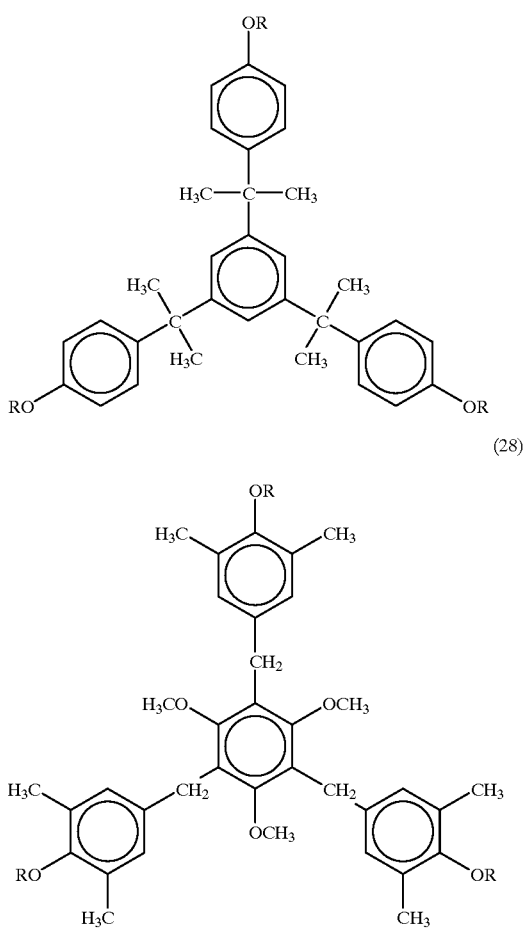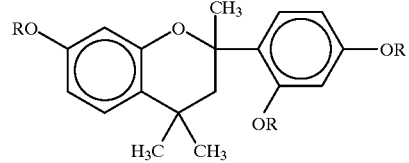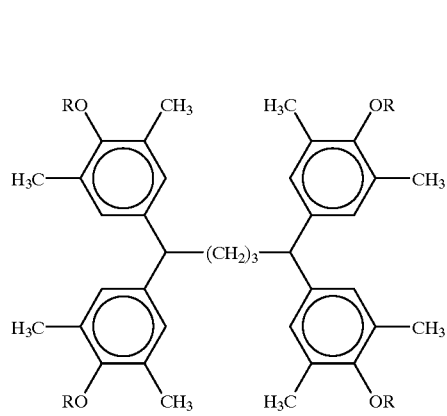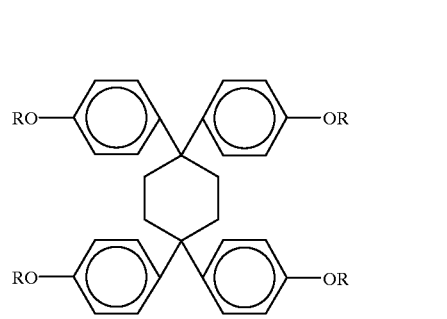

(36)
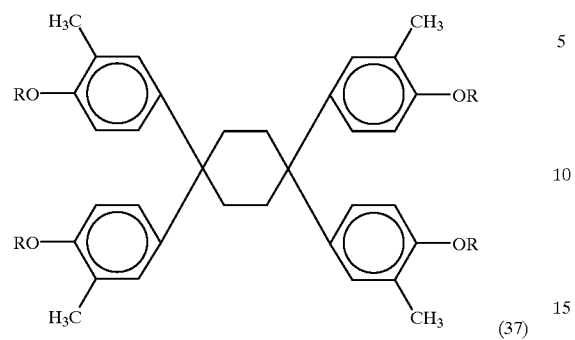
(37)
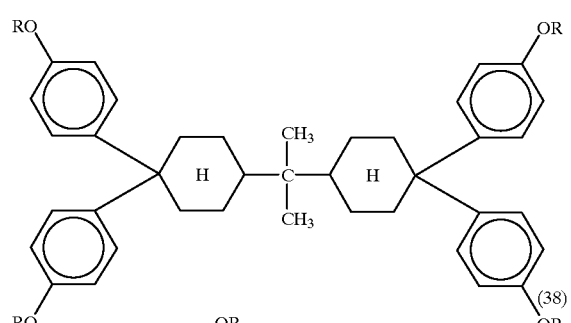
(38)
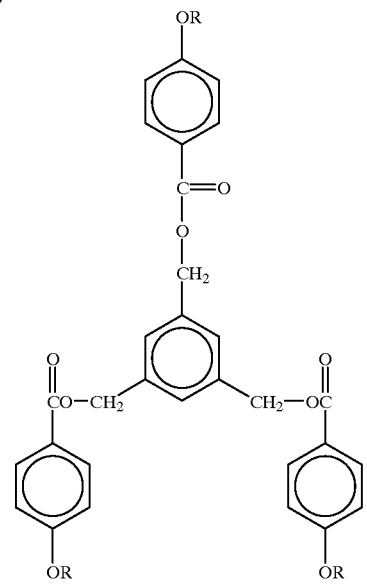
(39)
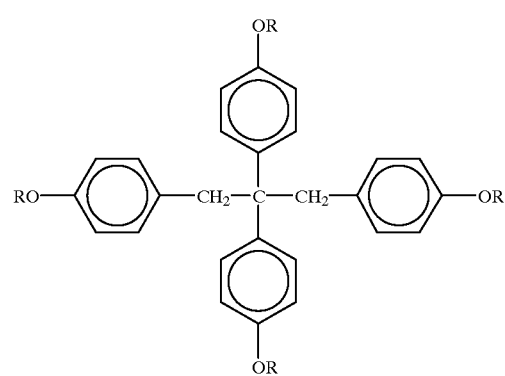
(40)
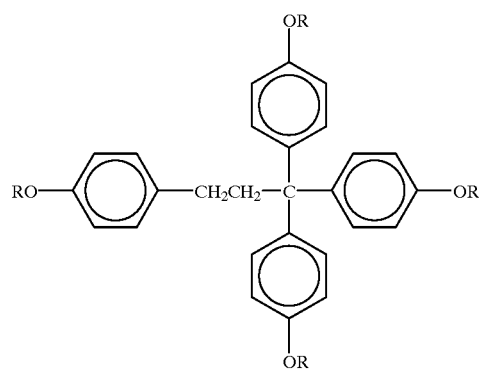
(41)
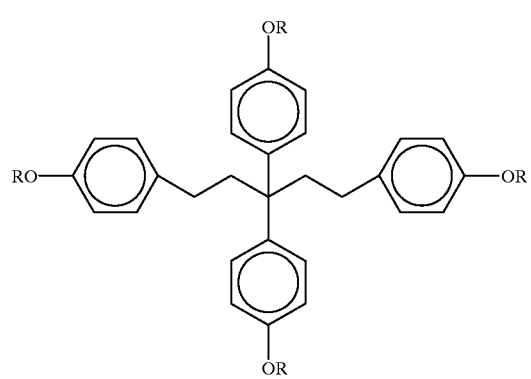
(42)
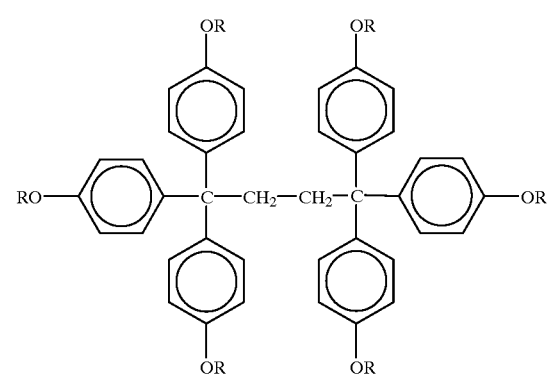
(43)
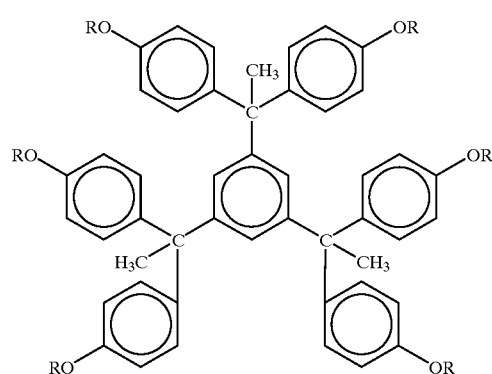

-continued

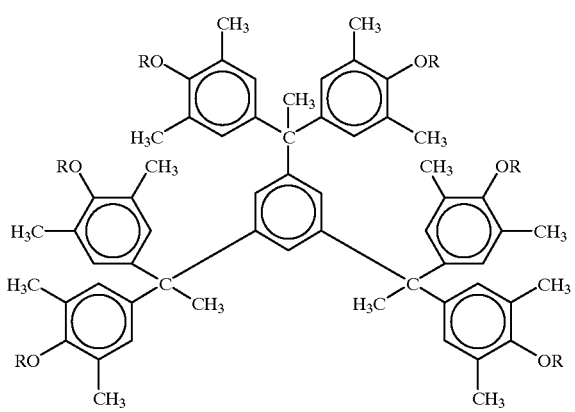
(44)

In the compounds (1) to (44) described above, R represents a hydrogen atom,

—$CH_2$—COO—$C(CH_3)_2C_6H_5$, —$CH_2$—COO—$C_4H_9^t$, —COO—$C_4H_9^t$,

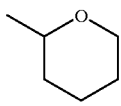

or —CH(L)—OZ (wherein L and Z each have the same meanings as those in the above-described formula (II)).

In addition, however, at least two R or three R according to the structure, represent groups other than a hydrogen atom, and each substituent R may not be a same group.

In the case of the 1st composition of the invention, the content of the component (D) is preferably from 3 to 45% by weight, more preferably from 5 to 30% by weight, and far more preferably from 10 to 20% by weight based on the solid components of the 1st composition.

In the case of the 2nd composition of the invention, the content of the component (D) is same as the case of the above-described 1st component.

[5] (E) Alkali-soluble Resin (Component (E))

The alkali-soluble resin (E) is the indispensable component of the 2nd composition of the invention. The alkali-soluble resin (E) is a component, which may be added to the 1st component of the invention. The alkali-soluble resin (E) is a resin, which is insoluble in water and soluble in an alkali developer, and is used for controlling the alkali-solubility of the 2nd composition of the invention. The resin (E) does not substantially have a group decomposable with acid.

The component (E) includes, for example, a novolac resin, a hydrogenated novolac resin, an acetone-pyrogallol resin, o-polyhydroxystyrene, m-polyhydroxystyrene, p-polyhydroxystyrene, hydrogenated polyhydroxystyrene, a halogen- or alkyl-substituted polyhydroxystyrene, a hydroxystyrene-N-substituted maleimide copolymer, an o/p- or m/p-hydroxystyrene copolymer, a partially alkylated product to the hydroxy group of polyhydroxystyrene (for example, the 5 to 30 mol % o-methylated product, o-(1-methoxy)ethylated product, o-(1-ethoxy)ethylated product, o-2-tetrahydropyranylated product, o-(t-butoxycarbonyl) methylated product, etc.), or the o-acylated product (for example, the 5 to 30 mol % o-acetylated product, o-(t-butoxy)carbonylated product, etc.), a styrene-maleic anhydride copolymer, a styrene-hydroxystyrene copolymer, an α-methylstyrene-hydroxystyrene copolymer, a carboxy group-containing methacrylic resin and the derivatives thereof, and polyvinyl alcohol derivatives, but the invention is not limited to these compounds.

The particularly preferred alkali-soluble resin (E) includes a novolac resin, o-polyhydroxystyrene, m-polyhydroxystyrene, p-polyhydroxystyrene, and the copolymers thereof, an alkyl-substituted polyhydroxystyrene, the partially o-alkylated or o-acylated product of polyhydroxystyrene, a styrene-hydroxystyrene copolymer, an α-methylstyrene-hydroxystyrene copolymer, a di- or tri-alkoxystyrene-hydroxystyrene copolymer.

The novolac resin described above is obtained by addition-condensing a definite monomer as the main constituent with an aldehyde in the existence of an acidic catalyst.

The weight average molecular weight of the novolac resin is in the range of preferably from 1,000 to 30,000. When the molecular weight is less than 1,000, the film reduction of the non-irradiated portions after development is large, while when the molecular weight exceeds 30,000, the development speed is delayed. The particularly preferred weight average molecular weight is in the range of from 2,000 to 20,000.

Also, the weight average molecular weight of the above-described polyhydroxystyrene, the derivatives thereof, and copolymers other than the novolac resin is at least 2,000, preferably from 5,000 to 20,000, and more preferably from 8,000 to 100,000. Also, from the view point of improving the heat resistance of the resist film, the molecular weight is preferably at least 10,000.

In this case, the weight average molecular weight is defined by the polystyrene-converted value of a gel permeation chromatography.

The alkali-soluble resins in the invention may be used singly or as a mixture of two or more kinds thereof.

The using amount of the alkali-soluble resin (E) is preferably from 40 to 97% by weight, and more preferably from 60 to 90% by weight based on the solid components of the 2nd composition of the invention.

[6] (F) Nitrogen-containing Basic Compound (Component (F))

The preferred nitrogen-containing basic compound, in the positive resist composition of the invention, is a compound having a stronger basic property than phenol. In these compounds, the nitrogen-containing compounds containing the structures represented by following formulae (A) to (E) are preferred. By using the nitrogen-containing basic compound, the performance change with the passage of time from the irradiation to heating is less.

(A)

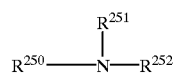

wherein, $R^{250}$, $R^{251}$, and $R^{252}$, which are the same or different, each represents a hydrogen atom, an alkyl group having from 1 to 6 carbon atoms, an aminoalkyl group having from 1 to 6 carbon atoms, a hydroxyalkyl group having from 1 to 6 carbon atoms, or a substituted or unsubstituted aryl group having from 6 to 20 carbon atoms. Also, $R^{251}$ and $R^{252}$ may be bonded to each other to form a ring.

(B)

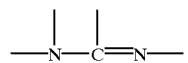

-continued

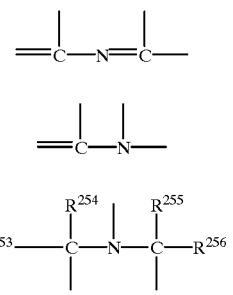

(wherein $R^{253}$, $R^{254}$, $R^{255}$, and $R^{256}$, which are the same or difference, each represents an alkyl group having from 1 to 6 carbon atoms.).

Preferred practical examples of the component (F) include a substituted or unsubstituted guanidine, a substituted or unsubstituted aminopyridine, a substituted or unsubstituted aminoalkylpyridine, a substituted or unsubstituted aminopyrrolidine, a substituted or unsubstituted indazole, a substituted or unsubstituted pyrazole, a substituted or unsubstituted pyrazine, a substituted or unsubstituted pyrimidine, a substituted or unsubstituted purine, a substituted or unsubstituted imidazoline, a substituted or unsubstituted pyrazoline, a substituted or unsubstituted piperazine, a substituted or unsubstituted aminomorpholine, a substituted or unsubstituted aminoalkylmorpholine, etc., and also include a mono-, di-, or tri-alkylamine, a substituted or unsubstituted aniline, a substituted or unsubstituted piperidine, a mono- or di-ethanolamine, etc.

The preferred substituent includes an amino group, an aminoalkyl group, an alkylamino group, an aminoaryl group, an arylamino group, an alkyl group, an alkoxy group, an acyl group, an acyloxy group, an aryl group, an aryloxy group, a nitro group, a hydroxy group, and a cyano group. Preferred compounds of the component (F) include guanidine, 1,1-dimethylguanidine, 1,1,3,3-tetramethylguanidine, 2-aminopyridine, 3-aminopyridine, 4-aminopyridine, 2-dimethylaminopyridine, 4-dimethylaminopyridine, 2-diethylaminopyridine, 2-(aminomethyl)pyridine, 2-amino-3-methylpyridine, 2-amino-4-methylpyridine, 2-amino-5-methylpyridine, 2-amino-6-methylpyridine, 3-aminoethyl-pyridine, 4-aminoethylpyridine, 3-aminopyrrolidine, piperazine, N-(2-aminoethyl)piperazine, N-(2-aminoethyl)piperidine, 4-amino-2,2,6,6-tetramethylpiperizine, 4-piperizinopiperizine, 2-iminopiperizine, 1-(2-aminoethyl) pyrrolidine, pyrazole, 3-amino-5-methylpyrazole, 5-amino-3-methyl-1-p-tolylpyrazole, pyrazine, 2-(aminomethyl)-5-methylpyrazine, pyrimidine, 2,4-diaminopyrimidine, 4,6-dihydroxypyrimidine, 2-pyrazoline, 3-pyrazoline, N-aminomorpholine, N-(2-aminoethyl)morpholine, 1,5-diazabicyclo[4,3,0]nona-5-ene, 1,8-diazabicyclo[5,4,0]-undeca-7-ene, 2,4,5-triphenylimidazole, tri(n-butyl)amine, tri(n-octyl)amine, N-phenyldiethanolamine, N-hydroxyethyl-piperidine, 2,6-diisopropylaniline, N-cyclohexyl-N'-morpholinoethyl thiourea, N-hydroxyethylmorpholine, etc., but the invention is not limited to these compounds.

In these compounds, the particularly preferred compounds include 1,5-diazabicyclo[4,3,0]nona-5-ene, 1,8-diazabicyclo-[5,4,0]undeca-7-ene, 2,4,5-triphenylimidazole, tri(n-butyl)-amine, tri(n-octyl)amine, N-phenyldiethanolamine, N-hydroxy-ethylpiperidine, 2,6-diisopropylaniline, N-cyclohexyl-N'-morpholinoethyl thiourea, and N-hydroxyethylmorpholine.

These nitrogen-containing basic compounds can be used singly or as a combination of two or more kinds thereof.

The using amount of the nitrogen-containing basic compound is usually from 0.001 to 10% by weight, and preferably from 0.01 to 5% by weight based on the solid components of the composition of the invention. When the using amount is less than 0.001% by weight, the effect of -adding the nitrogen-containing basic compound is not obtained. On the other hand, when the amount exceeds 10% by weight, there are tendencies that the sensitivity is lowered and the developing property of the non-irradiated portions is deteriorated.

[7] (G) A Surfactant Containing at Least one of the Group Consisting of a Fluorine Atom and a Silicon Atom (Component (G))

It is preferred that the positive resist composition of the invention contains the component (G).

The component (G) is at least one kind of surfactant selected from a surfactant containing a fluorine atom, a surfactant containing a silicon atom, and a surfactant containing both a fluorine atom and a silicon atom.

By containing the above-described surfactant in the positive resist composition of the invention, at using an exposure light source of a wavelength of not longer than 250 nm, and particularly not longer than 220 nm, the resist composition is excellent in the sensitivity, the resolving power, the adhesion with a substrate, and a dry etching resistance, the generation of particles after storing for a long period of time is less, and further resist patterns having less development defects and scum are obtained.

As these surfactants, there are the surfactants described, for example, in Japanese Patent Laid-Open Nos. 36663/1987, 226746/1986, 226745/1986, 170950/1987, 34540/1988, 230165/1995, 62834/1996, 54432/1997, and 5988/1997, U.S. Pat. Nos. 5,405,720, 5,360,692, 5,529,881, 5,296,330, 5,436,098,5,576,143, 5,294,511, and 5,824,451, and also the following commercially available surfactants can be used as they are.

As the commercially available surfactants, which can be used in the invention, there are the fluorine-containing surfactants and the silicon-containing surfactants, such as, for example, Eftop EF301 and EF303 (manufactured by Shin Akita Kasei K.K.), Florad FC430 and 431 (manufactured by SUMITOMO 3M INC.), Megafac F171, F173, F176, F189, and R08 (manufactured by DAINIPPON INK & CHEMICALS, INC.), Surflon S-301, 102, 103, 104, 105, and 106 (manufactured by Asahi Glass Company Ltd.), and Troysol S-366 (manufactured by Troy Chemical Industry K. K.). Also, the polysiloxane polymer KP-341 (manufactured by Shin-Etsu Chemical Co., Ltd.) can be used as a silicon-containing surfactant.

The amount of the surfactant (G) is usually from 0.001 to 2% by weight, and preferably from 0.01 to 1% by weight based on the solid components in the composition of the invention. These surfactants may be used singly or as a combination of two or more kinds thereof.

[8] Other Components Used in the Invention

The positive photosensitive composition of the invention can, if necessary, further comprising a dye, a pigment, plasticizer, other surfactant than those described above, a photosensitizer, a compound having at least two phenolic OH groups of accelerating the solubility in a developer, etc.

The compound having at least two phenolic OH groups, which can be used in the invention, is preferably a phenol compound having a molecular weight of not larger than 1000. Also, it is necessary that the compound contains at least two phenolic hydroxy groups in the molecule but the number of the phenolic hydroxy groups exceeds 10, the effect of improving the development latitude is lost. The ratio of the phenolic hydroxy groups and the aromatic rings is preferably from 0.5 to 1.4, and, thereby, the film thickness dependency, development latitude, the stability of the composition, and resolving power are excellent.

The addition amount of the phenol compound is preferably from 2 to 50% by weight, and more preferably from 5 to 30% by weight to the alkali-soluble resin. When the addition amount exceeds 50% by weight, the development residue becomes bad and a new fault that the pattern is deformed at development undesirably occurs.

The phenol compounds having a molecular weight of not larger than 1000 can be easily synthesized by persons skilled in the art by referring to the methods described, for example, in Japanese Patent Laid-Open Nos. 122938/1992 and 28531/1990, U.S. Pat. No. 4,916,210, European Patent 219294, etc.

Practical examples of the phenol compound are shown below but the phenol compounds, which can be used in the invention, are not limited to them.

That is, the practical examples of the phenolic compound include resorcinol, phloroglucine, 2,3,4-trihydroxybenzophenone, 2,3,4,4'-tetrahydroxybenzophenone, 2,3,4,3',4',5'-hexahydroxybenzophenone, acetone-pyrogallol condensed resin, fluoroglucoside, 2,4,2',4'-biphenyltetrole, 4,4'-thiobis(1,3-dihydroxy)benzene, 2,2',4,4'-tetrahydroxydiphenyl ether, 2,2',4,4'-tetrahydroxydiphenyl sulfoxide, 2,2',4,4'-tetra-hydroxydiphenylsulfone, tris(4-hydroxyphenyl)methane, 1,1-bis(4-hydroxyphenyl)cyclohexane, 4,4-($\alpha$-mehylbenzylidene)-bisphenol, $\alpha,\alpha',\alpha''$-tris(4-hydroxyphenyl)-1,3,5-triisopropyl-benzene, $\alpha,\alpha',\alpha''$-tris(4-hydroxyphenyl)-1-ehyl-4-isopropyl-benzene, 1,2,2-tris(hydroxyphenyl)propane, 1,1,2-tris(3,5-dimethyl-4-hydroxyphenyl)propane, 2,2,5,5-tetrakis(4-hydroxy-phenyl)hexane, 1,2-tetrakis(4-hydroxyphenyl)ethane, 1,1,3-tris(hydroxyphenyl)butane, para[$\alpha,\alpha,\alpha',\alpha'$-tetrakis(4-hydroxyphenyl)]-xylene, etc.

Preparation of Positive Resist Composition and the Use Thereof

Each component contained in the positive resist compositions of the invention was explained above. Then, the preparation method of the positive resist composition of the invention and the using method thereof are explained.

In the composition of the invention, each component described above is dissolved in a solvent dissolving the component and the solution prepared is coated on a support.

The solvent used in the case includes ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, ethylene glycol monoethyl ether acetate, propylene glycol monomethyl ether, propylene glycol monomethyl ether acetate, toluene, ethyl acetate, methyl lactate, ethyl lactate, methyl methoxypropionate, ethyl ethoxypropionate, methyl pyruvate, ethyl pyruvate, propyl pyruvate, N,N-dimethylformamide, dimethyl sulfoxide, N-methylpyrrolidone, tetrahydrofuran, etc. These solvents may be used solely or as a mixture thereof.

In these solvents, the preferred solvents include 2-heptanone, γ-butyrolactone, ethylene glycol monomethyl ether, ethylene glycol monoethyl ether, ethylene glycol monoethyl ether acetate, propylene glycol monomethyl ether, propylene glycol monomethyl ether acetate, propylene glycol monoethyl ether acetate, methyl lactate, ethyl lactate, methyl methoxypropionate, ethyl ethoxypropionate, N-methylpyrrolidone, tetrahydrofuran, etc.

In this case, it is preferred to add the above-described fluorine-base and/or silicon-base surfactant (G) to the above-described solvent.

Also, other surfactant than the component (G) can be added. Such a surfactant includes nonionic surfactants, for example, polyoxyethylene alkyl ethers such as polyoxyethylene lauryl ether, polyoxyethylene stearyl ether, polyoxyethylene cetyl ether, polyoxyethylene oleyl ether, etc.; polyoxyethylene alkylaryl ethers such as polyoxyethylene octylphenol ether, polyoxyethylene nonylphenol ether, etc.; polyoxyethylene•polyoxypropylene block copolymers; sorbitan fatty acid esters such as sorbitan monolaurate, sorbitan monopalmitate, sorbitan monostearate, sorbitan monooleate, sorbitan trioleate, sorbitan tristearate, etc; polyoxyethylene-sorbitan fatty acid esters such as polyoxyethylenesorbitan monopalmitate, polyoxyethylenesorbitan monostearate, polyoxyethylenesorbitan trioleate, polyoxyethylenesorbitan tristearate, etc,; and also acrylic acid-base or methacrylic acid-base (co)polymers, Polyflow No. 75 and No. 95 (manufactured by Kyoeisha Yushi Kagakukogyo K.K.), etc.

The compounding amount of the surfactant is usually not larger than 2 parts by weight, and preferably not larger than 1 part by weight per 100 pats by weight of the solid components in the composition of the invention.

After coating the above-described composition on a substrate (for example, silicon, silicon dioxide coating, and titanium nitride) as used for the production of precise integrated circuit devices or on such a substrate having formed thereon an anti-reflection film having a thickness of from 100 to 2,000 A, the coated film is light-exposed through a definite mask, or a direct imaging by electron beam or a mask-irradiation of electron beam is applied to the coated film, and by carrying out baking and development, good resist patterns can be obtained.

As the developer of the composition of the invention, an alkaline aqueous solution of inorganic alkalis such as sodium hydroxide, potassium hydroxide, sodium carbonate, sodium silicate, sodium metasilicate, aqueous ammonia, etc.; primary amines such as ethylamine, n-propylamine, etc.; secondary amines such as diethylamine, di-n-butylamine, etc.; tertiary amines such as triethylamine, methyldiethylamine, etc.; alcoholamines such as dimethyl ethanolamine, triethanolamine, etc.; quaternary ammonium salts such as tetramethylammonium hydroxide, tetraethylammonium hydroxide, etc.; cyclic amines such as pyrrole, piperidine, etc., can be used.

Furthermore, proper amounts of an alcohol and a surfactant can be added to the above-described alkaline aqueous solution.

EXAMPLES

Then, the present invention is practically described by the following examples but the scope of the invention is not limited by these examples.

Synthesis of Component (A)

Synthesis of (IV-1):

In 400 ml of methanol was dissolved 20 g of triphenylsulfonium iodide, and after adding thereto 12.5 g of silver oxide, the mixture was stirred at room temperature (about 23° C.) for 4 hours. From the reaction liquid, a silver compound was removed by filtration, and 9.9 g of saccharin was added to the filtrate. When the solution was concentrated and the solids obtained were washed with 300 ml of ethyl acetate, 22 g of the compound (IV-1) was obtained. M.P.: 147 to 149° C., 300 MHz $^1$H-NMR: δ7.35 to 7.4 (m. 2H), δ7.5 to 7.7 (m. 17H).

Synthesis of (IV-2):

By following the same procedure as the synthesis of (IV-1) using p-t-butylphenyldiphenylsulfonium iodide in place of triphenylsulfonium iodide, t-butylphenyldiphenylsulfonium saccharinate (IV-2) was synthesized.

Synthesis of (IV-3):

By following the same procedure as the synthesis of (IV-1) using p-methylphenylphenyldiphenylsulfonium iodide in place of triphenylsulfonium iodide, p-methylphenyldiphenylsulfonium saccharinate (IV-3) was synthesized.

Synthesis of (IV-4):

By following the same procedure as the synthesis of (IV-1) using tris (t-butylphenyl) sulfonium iodide in place of triphenylsulfonium iodide, tris(t-butylphenyl)sulfonium saccharinate (IV-4) was synthesized.

Synthesis of (IV-5):

By following the same procedure as the synthesis of (IV-1) using bis(p-chlorophenyl)phenylsulfonium iodide in place of triphenylsulfonium iodide, bis(p-chlorophenyl) phenylsulfonium saccharinate (IV-5) was synthesized.

Synthesis of (IV-6):

By following the same procedure as the synthesis of (IV-1) using p-n-butoxyphenyldiphenylsulfonium iodide in place of triphenylsulfonium iodide, p-n-butoxyphenyldiphenylsulfonium saccharinate (IV-6) was synthesized.

Synthesis of (V-1):

In 300 ml of methanol was dissolved 10 g of bis[(4-diphenylsulfonio)phenyl]sulfide bisiodide, and after adding thereto 6.0 g of silver oxide (I), the mixture was stirred at room temperature (about 23° C.) for 4 hours. From the reaction liquid, a silver compound was removed by filtration, and 4.8 g of saccharin was added to the filtrate obtained. When the solution was concentrated and washed with 300 ml of di-isopropyl ether, 6 g of the compound (V-1) was obtained.

Synthesis of (VI-1):

After mixing 100 g of bis(4-t-amylphenyl)iodonium iodide and 2000 ml of methanol, 44.4 g of silver oxide was added to the mixture, and resultant mixture was stirred at room temperature (about 23° C.) for 4 hours. From the reaction liquid, a silver compound was removed by filtration, and 35.2 g of saccharin was added to the filtrate obtained. When the solution was concentrated and 700 ml of ethyl acetate was added to the oily material obtained, solids were precipitated. When the solids were collected by filtration and washed with 700 ml of ethyl acetate, 55 g of the compound (VI-1) was obtained. M.p.: 152 to 155° C., 300 MHz $^1$H-NMR: $\delta$0.6(t. 6H), $\delta$1.15(s. 12H), $\delta$1.55(q. 4H), $\delta$7.3(d. 4H), $\delta$7.4 to 7.5(m. 2H), $\delta$7.6 to 7.7(m. 2H), $\delta$7.8(d. 2H).

Synthesis of (VI-2):

By following the same procedure as the synthesis of (VI-1) using bis (4-t-butylphenyl) iodonium iodide in place of bis(4-t-amylphenyl)iodonium iodide, bis(4-t-butylphenyl)-iodonium saccharinate (VI-2) was synthesized.

Synthesis of (VI-3):

By following the same procedure as the synthesis of (VI-1) using diphenyliodonium iodide in place of bis(4-t-amylphenyl)-iodonium iodide, diphenyliodonium saccharinate (VI-3) was synthesized.

Other compounds were also synthesized using the similar methods.

Synthesis of Component (B)

(1) <Synthesis of p-(1-(cyclohexyletoxy)ethoxy)styrene/p-hydroxystyrene (30/70)(Resin A-25)>

In 320 g of propylene glycol monomethyl ether acetate (PGMEA) was dissolved 70 g of poly p-hydroxystyrene (VP-8000 manufactured by Nippon Soda Co., Ltd., weight average molecular weight 1000) by heating and after dehydrating by a vacuum distillation, the solution was cooled to 20° C. To the solution were added 0.35 g of pyridinium-p-toluene sulfonate and 22.4 g of cyclohexane ethanol. Then, 17.5 g of t-butyl vinyl ether was slowly added to the solution and the reaction was carried out at 20° C. for 5 hours. To the reaction liquid were added 0.28 g of triethylamine and 320 ml of ethyl acetate, and the mixture was washed 3 times with 150 ml of distilled water. Thereafter, the solvent was distilled off and the residue was concentrated. The oil obtained was dissolved in 100 ml of acetone and the solution was slowly poured to 2 liter of distilled water. When the powder precipitated was collected by filtration and dried, 54 g of the desired product was obtained.

(2) <Synthesis of p-(1-(cyclohexylethoxy)ethoxy)-styrene/ p-acetoxystyrene/p-hydroxystyrene (30/10/60) (Resin A-38)>

In 320 g of propylene glycol monomethyl ether acetate (PGMEA) was dissolved 70 g of poly p-hydroxystyrene (VP-8000, manufactured by Nippon Soda Co., Ltd. , weight average molecular weight 1000) by heating, and after dehydrating by a vacuum distillation, the solution was cooled to 20° C. To the solution were added 0.35 g of pyridinium-p-toluene sulfonate and 22.4 g of cyclohexane ethanol. After slowly adding 17.5 g of t-butyl vinyl ether to the solution, the reaction was carried out at 20° C. for 5 hours. To the reaction liquid was added 5.53 g of pyridine and then 5.9 g of acetic anhydride was slowly added to the mixture. Thereafter, the reaction was carried out at room temperature for 1 hour, and after adding 320 ml of ethyl acetate to the reaction liquid, the mixture was washed 3 times with 150 ml of distilled water. Then, the solvent was distilled off and the residue was concentrated. The oil obtained was dissolved in 100 ml of acetone and the solution obtained was slowly poured into 2 liters of distilled water. When the powder precipitated was collected by filtration and dried, 58 g of the desired product was obtained.

(3) By using the methods similar to the methods (1) and (2) described above, the following resins were synthesized.

A-3: p-(1-Ethoxyethoxy)styrene/p-hydroxystyrene (35/65), molecular weight: 15,000, dispersion degree (Mw/Mn): 1.1.

A-7: p-(1-iso-butoxyethoxy)styrene/p-hydroxystyrene (30/70), molecular weight: 6000, dispersion degree (Mw/Mn) 1.2.

A-36: p-(1-phenetyloxyethoxy)styrene/p-acetoxystyrene/ p-hydroxystyrene (30/10/60), molecular weight: 11000, dispersion degree (Mw/Mn): 1.2.

A-41: p-(1-(4-t-Butylcyclohexylcarboxyethoxy) ethoxystyrene/p-acetoxystyrene/p-hydroxystyrene (30/10/60), molecular weight:12000, dispersion degree (Mw/Mn): 1.1.

A-43: p-(1-(cyclohexylethoxy)ethoxy)styrene/p-t-butyl-styrene/p-hydroxystyrene (30/8/62), molecular weight: 1800, dispersion degree (Mw/Mn): 2.3.

A-22: p-(1-Benzyloxyethoxy)styrene/p-hydroxystyrene (25/75), molecular weight: 13000, dispersion degree (Mw/Mn) 1.3.

A-35: p-(1-Benzyloxyethoxy)styrene/p-hydroxystyrene/ p-acetoxystyrene (20/70/10), molecular weight: 9000, dispersion degree (Mw/Mn): 1.2.

Furthermore, the following resins as the components (A) were synthesized.

(4) <Synthesis of A-48: p-hydroxystyrene/t-butyl acrylate (79/21)>

In 150 g of dioxane were dissolved 84.1 g of p-vinyl phenol and 22.4 g of t-butyl acrylate and a nitrogen gas stream was introduced into the system.

Then, 6.91 g of dimethyl 2,2'-azobisisobutyrate was added to the solution, and the mixture was heated to 75° C. under a nitrogen gas stream to carry out the polymerization for 12 hours. After the polymerization was finished, the reaction liquid was cooled to room temperature, after diluting the reaction liquid by adding 150 g of acetone, the solution was added dropwise to a large amount of hexane to obtain a solid polymer. The dilution with acetone and adding to hexane were repeated 3 times to remove residual monomers.

By vacuum drying the polymer obtained at 60° C., the polymer A-48 was obtained.

As the result of the analysis by NMR, the composition ratio of p-vinyl phenol:t-butyl acrylate was 79:21.

The Mw was 12,000 and the dispersion degree (Mw/Mn) was 2.6.

(5) <Synthesis of A-16; p-(1-iso-butoxyethoxy)styrene/p-hydroxystyrene/t-butyl acrylate (20/59/21)>

In 80 g of propylene glycol monoethyl ether acetate (PGMEA) was dissolved 20 g of the above-described polymer (A-48), after heating the solution to 60° C., the pressure of the system was gradually reduced to 20 mmHg, and PGMEA and water in the system were azeotropically dehydrated. After the azeotropic dehydration, the solution was cooled to 20° C., 2.2 g of isobutyl vinyl ether was added, and further, 3 mg of p-toluenesulfonic acid was added. Thereafter, the reaction was carried out for 2 hours, and the acid was neutralized by the addition of a small amount of triethylamine. Thereafter, ethyl acetate was added to the reaction liquid and by washing with ion-exchanged water, salts were removed. Furthermore, by distilling off ethyl acetate and water from the reaction liquid under a reduced pressure, the polymer A-16 as the desired product was obtained.

(6) A-51; p-hydroxystyrene/styrene/t-butyl acrylate (78/7/15)(molecular weight 13100, dispersion degree (Mw/Mn) 2.7) was synthesized by a method similar to the synthesis of the above-described resin A-48.

(7) <Synthesis A-49; p-hydroxystyrene/p-(t-butoxycarbonyloxy)styrene (60/40)>

In 40 ml of pyridine was dissolved poly p-hydroxystyrene (VP-8000, manufactured by Nippon Soda Co., Ltd., weight average molecular weight 1000), and 1.28 g of di-t-butyl dicarbonate was added to the solution with stirring at room temperature. After carrying out the reaction at room temperature for 3 hours, the reaction liquid was added to a solution of 1 liter of ion-exchanged water and 20 g of concentrated hydrochloric acid. The powder precipitated was collected by filtration, washed with water, and dried to obtain a p-hydroxystyrene/p-(t-butyloxycarbonyloxy)-styrene copolymer (60/40).

Examples 1 to 31 and Comparative Examples 1 and 2

According to the compositions shown in Table 1 below, each component was dissolved in a solvent (ratio of each solvent was denoted by weight in mixed solvent), the solid component concentration was controlled to 15% by weight in each case, and each solution was filtered by a polyethylene filter of 0.1 $\mu$m to prepare each resist solution. About the resist solutions, the following evaluations were carried out.

A. KrF Excimer laser exposure evaluation:

Each resist solution was uniformly coated on a silicon wafer subjected to a hexamethyldisilazane treatment using a spin coater and heat-dried on a hot plate at 120° C. for 90 seconds to form a resist film of 0.6 $\mu$m thick. The resist film was pattern-exposed using a KrF excimer laser stepper (NA=0.63) and using a mask for line and space, and immediately after the exposure, the resist film was heated on a hot plate at 110° C. for 90 seconds. Then, the resist film was developed with an aqueous solution of 2.38% by weight tetramethylammonium hydroxide at 23° C. for 60 seconds and after rinsing with pure water for 30 seconds, the resist film was dried. From the patterns on the silicon wafer obtained as described above, the performance of the resist was evaluated by the following methods. The results are shown in Table 2 below.

Resolving Power

The limiting resolving power in an exposure amount necessary for reproducing a mask pattern of line and space (1/1) of 0.18 $\mu$m was measured.

Exposure Margin

The exposure amount necessary for reproducing a mask pattern of line and space (1/1) of 0.16 $\mu$m is defined the optimum exposure amount, and a value of the exposure amount width of reproducing a line width of 0.16 $\mu$m±10% divided by the optimum exposure amount was shown by percent (%). As the numeral is larger, a change of the line width owing to the change of exposure amount is less.

Depth of Focus

The depth of focus of line and space (1/1) of 0.15 $\mu$m in an exposure amount necessary for reproducing a mask pattern of line and space (1/1) of 0.15 $\mu$m was measured. As the value is larger, the depth of focus is broader.

TABLE 1

| Example | Resin (B) | Component (A) | Component (C) | Component (D) | Basic compound (F) | Surfactant (G) | Solvent |
|---|---|---|---|---|---|---|---|
| 1 | (A-3) 10 g | (IV-16) 0.6 g | | | (1) 0.025 g | (W1) 0.03 g | PGMEA |
| 2 | (A-7) 10 g | (IV-17) 0.5 g | | | (2) 0.025 g | (W2) 0.03 g | PGMEA |
| 3 | (A-14) 10 g | (IV-18) 0.4 g | | | (3) 0.025 g | (W3) 0.03 g | PGMEA |
| 4 | (A-16) 10 g | (IV-1) 0.3 g | (PAG4-1) 0.4 g | | (4) 0.025 g | (W4) 0.03 g | PGMEA |
| 5 | (A-25) 10 g | (IV-2) 0.4 g | (PAG3-2) 0.4 g | | (1) 0.03 g | (W1) 0.03 g | PGMEA |
| 6 | (A-36) 10 g | (IV-3) 0.3 g | (PAG3-1) 0.3 g | | (2) 0.05 g | (W4) 0.03 g | PGMEA |
| 7 | (A-38) 10 g | (IV-4) 0.2 g | (PAG3-3) 0.4 g | | (2) 0.02 g | (W2) 0.03 g | PGMEA |
| 8 | (A-41) 10 g | (IV-8) (V-1)* 0.2 g | (PAG4-1) 0.4 g | | (2) 0.025 g | (W4) 0.05 g | PGMEA/PGME = 8/2 |
| 9 | (A-43) 10 g | (IV-5) 0.1 g | (PAG4-3) 0.6 g | | (1) 0.025 g | (W1) 0.03 g | EL/EEP = 8/2 |
| 10 | (A-48) 10 g | (IV-6) 0.2 g | (PAG4-4) 0.4 g | | (1) 0.025 g | (W4) 0.03 g | EL/EEP = 8/2 |
| 11 | (A-49) 10 g | (IV-7) 0.3 g | (PAG3-2) 0.2 g | | (4) 0.015 g | (W2) 0.03 g | EL/EEP = 8/2 |

TABLE 1-continued

| | Resin (B) | Component (A) | Component (C) | Component (D) | Basic compound (F) | Surfactant (G) | Solvent |
|---|---|---|---|---|---|---|---|
| 12 | (A-51) 10 g | (IV-9) 0.5 g | (PAG4-1) 0.1 g | | (3) 0.01 g | (W4) 0.05 g | EL/EEP = 8/2 |
| 13 | (A-3) 10 g | (IV-11) 0.2 g | (PAG7-1) 0.2 g (PAG7-1) 0.4 g | | (2) 0.02 g | (W4) 0.05 g | PGMEA/PGME = 8/2 |
| 14 | (A-7) 10 g | (VI-1) 0.3 g | (PAG6-2) 0.6 g | | (2) 0.025 g | (W4) 0.05 g | EL/EEP = 8/2 |
| 15 | (A-22) 10 g | (VI-2) 0.2 g | (PAG7-3) 0.5 g | | (1) 0.025 g | (W2) 0.03 g | EL/EEP = 8/2 |
| 16 | (A-25) 10 g | (VI-7) 0.1 g | (PAG4-4) 0.2 g (PAG7-2) 0.3 g | | (1) 0.025 g | (W2) 0.03 g | CH |
| 17 | (A-36) 10 g | (IV-1) 0.1 g | (PAG7-1) 0.2 g (PAG7-1) 0.4 g | | (4) 0.005 g | (W4) 0.05 g | PGMEA/PGME = 8/2 |
| 18 | (A-38) 10 g | (IV-1) 0.2 g | (PAG4-4) 0.2 g (PAG4-5) 0.2 g | | (3) 0.005 g | (W1) 0.03 g | PGMEA/PGME = 8/2 |
| 19 | (A-41) 10 g | (IV-1) 0.2 g | (PAG4-4) 0.4 g | | | (W2) 0.03 g | PGMEA/PGME = 8/2 |
| 20 | (A-43) 10 g | (VI-1) 0.3 g | (PAG4-4) 0.2 g (PAG7-2) 0.3 g | | | (W3) 0.03 g | PGMEA/PGME = 8/2 |
| 21 | (A-35) 10 g | (VI-1) 0.3 g | (PAG4-4) 0.2 g (PAG4-5) 0.2 g | | | (W4) 0.03 g | PGMEA/PGME = 8/2 |
| 22 | (A-48) 9 g | (VI-1) 0.2 g | (PAG4-4) 0.4 g | (D-1) 1 g | (1) 0.025 g (2) 0.025 g | (W1) 0.03 g | PGMEA/PGME = 8/2 |
| 23 | (A-49) 10 g | (VI-1) 0.3 g | (PAG4-4) 0.2 g (PAG4-5) 0.2 g | | (2) 0.1 g | (W4) 0.03 g | PGMEA/PGME = 8/2 |
| 24 | (A-51) 3 g | (VI-1) 0.2 g | (PAG4-4) 0.4 g | (D-1) 1 g | (1) 0.06 g | (W2) 0.03 g | PGMEA/PGME = 8/2 |
| 25 | (A-25) 10 g | (VI-1) 0.3 g | (PAG4-4) 0.2 g (PAG7-2) 0.3 g | | (1) 0.025 g | (W4) 0.05 g | PGMEA/BL = 8/2 |
| 26 | (A-36) 10 g | (VI-1) 0.2 g | (PAG4-4) 0.5 g | | (1) 0.025 g | (W1) 0.03 g | PGMEA |
| 27 | (A-38) 10 g | (V-3) 0.2 g | (PAG4-4) 0.5 g | | (4) 0.015 g | (W4) 0.03 g | PGMEA |
| 28 | (A-41) 10 g | (V-1) 0.3 g | (PAG4-4) 0.5 g | | (3) 0.01 g | (W2) 0.03 g | PGMEA |
| 29 | (A-43) 10 g | (V-1) 0.2 g | (PAG4-4) 0.4 g | | (2) 0.02 g | (W4) 0.05 g | PGMEA |
| 30 | (A-25) 10 g | (IV-1) 0.5 g | (PAG4-4) 0.5 g | | (1) 0.025 g | (W4) 0.05 g | PGMEA |
| 31 | PHS/ST | (IV-1) 0.5 g | (PAG4-4) 0.6 g | (D-1) 1 g | (1) 0.025 g | (W4) 0.05 g | PGMEA |
| Comparat. Example | | | | | | | |
| 1 | (A-3) 10 g | | (PAG4-1) 0.5 g | | (1) 0.025 g | (W1) 0.03 g | PGMEA |
| 2 | (A-51) 9 g | | (PAG4-4) 0.4 g | (D-1) 1 g | (1) 0.06 g | (W2) 0.03 g | PGMEA/BL = 8/2 |

(IV-8)/(V-1)*: Mixture containing (IV-8) and (V-1) as the main constituents.
Comparat.: Comparative Explanation of the Components of Table 1
Component (A):
Example 8: A mixture of (IV-8) and (V-1) as the main constituents was used as the component (A) Component (B)(the amount is indicated the value as solid components)
PHS/ST of Example 31 denotes a p-hydroxystyrene/styrene (85:15 by mol ratio) copolymer (weight average molecular weight: 20,000, dispersion degree: 2.9), which is an alkali-soluble resin. Component (D)
(D-1): Compound having the Following Structure.

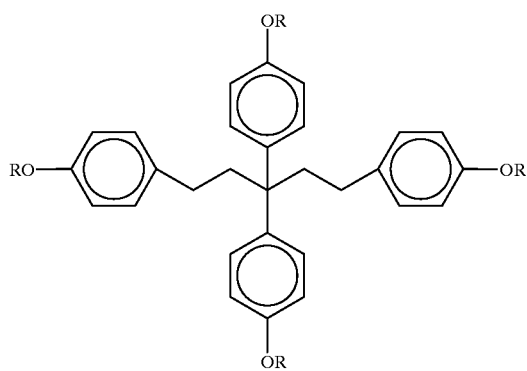

(D-1)

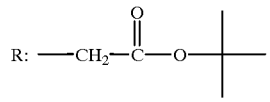

(F) Basic Compound Component:
(1): 1,5-Diazabicyclo[4,3,0]-5-nonene
(2): 2,4,5-Triphenylimidazole
(3): Tri-n-butylamine
(4): N-Hydroxyethylpiperidine (G) Surfactant Component:
W-1: Megafac F176 (manufactured by DAINIPPON INK & CHEMICALS INC.)(fluorine-containing)
W-2: Megafac R08 (manufactured by DAINIPPON INK & CHEMICALS INC.)(fluorine- and silicon-containing)
W-3: Polysiloxane polymer KP-341 (manufactured by Shin-Etsu Chemical Co., Ltd)
W-4: Troysol S-366 (manufactured by Troy Chemical Industry Inc.)

Solvent:
PGMEA: Propylene glycol monomethyl ether acetate
PGME: Propylene glycol monomethyl ether (1-methoxy-2-propanol)

EL: Ethyl lactate
EEP: Ethyl ethoxypropionate
BL: γ-Butyrolactone
CH: Cyclohexane Ratio in the case of using mixed solvents is indicated by a weight.

TABLE 2

| | Resolving Power (μm) | Exposure Margin (%) | Depth of Focus (μm) |
|---|---|---|---|
| Example | | | |
| 1 | 0.13 | 10.0 | 1.0 |
| 2 | 0.13 | 9.5 | 0.9 |
| 3 | 0.13 | 10.0 | 1.0 |
| 4 | 0.125 | 10.0 | 1.2 |
| 5 | 0.125 | 12.0 | 1.5 |
| 6 | 0.125 | 11.5 | 1.4 |
| 7 | 0.125 | 12.0 | 1.5 |
| 8 | 0.125 | 12.5 | 1.5 |
| 9 | 0.125 | 10.0 | 1.0 |
| 10 | 0.125 | 9.8 | 1.0 |
| 11 | 0.125 | 11.0 | 1.1 |
| 12 | 0.125 | 10.0 | 1.2 |
| 13 | 0.13 | 10.2 | 1.2 |
| 14 | 0.13 | 10.1 | 1.2 |
| 15 | 0.125 | 11.5 | 1.4 |
| 16 | 0.125 | 12.0 | 1.5 |
| 17 | 0.125 | 12.5 | 1.4 |
| 18 | 0.125 | 11.5 | 1.5 |
| 19 | 0.125 | 12.0 | 1.5 |
| 20 | 0.13 | 9.8 | 1.2 |
| 21 | 0.13 | 9.9 | 1.2 |
| 22 | 0.14 | 8.0 | 1.0 |
| 23 | 0.14 | 7.8 | 1.1 |
| 24 | 0.14 | 8.1 | 1.0 |
| 25 | 0.125 | 12.0 | 1.4 |
| 26 | 0.125 | 12.5 | 1.5 |
| 27 | 0.125 | 11.5 | 1.5 |
| 28 | 0.125 | 12.0 | 1.4 |
| 29 | 0.125 | 11.5 | 1.5 |
| 30 | 0.125 | 12.0 | 1.5 |
| 31 | 0.14 | 8.0 | 0.9 |
| Comparative Example | | | |
| 1 | 0.14 | 4.2 | 0.6 |
| 2 | 0.14 | 3.4 | 0.4 |

From the results shown in Table 2, the following matters ear.

By irradiating the resist films of Examples 1 to 31, are the positive resist compositions of the invention with a KrF laser light, which is a far ultraviolet ray, patterns are formed with having a high resolving power, a broad exposure margin, and a broad depth of focus. On the other hand, in the cases of Comparative Examples 1 and 2 without using the component (A), the light-exposure margin and the depth of focus are narrow.

B. Electron Beam Irradiation Evaluation

A part of the examples described in Table 1 described above (the examples shown in Table 3 below) was controlled to the solid component concentration of 17% by weight to obtain each resist solution. The resist solution was uniformly coated on a silicon substrate subjected to a hexamethyldisilazane treatment by a spin coater, heated on a hot plate at 120° C. for 60 seconds, and dried to form a resist film of 0.8 μm thick. The resist film was irradiated by an electron beam imaging apparatus (accelerating voltage 50 kev, beam diameter 0.20 μm), and immediately after the irradiation, the resist film was heated on a hot plate to 110° C. for 90 seconds. Then, the resist film irradiated was developed with an aqueous solution of tetramethylammonium hydroxide at a concentration of 2.38% by weight at 23° C. for 60 seconds, and after rinsing with pure water for 30 seconds, the developed film was dried. From the patterns on the silicon wafer thus formed, the performance of the resist was evaluated by the following methods. The results are shown in Table 3 below.

Image Evaluation Method

A contact hole pattern of 0.2 μm formed was observed by a scanning electron microscope and the profile was determined.

Sensitivity Evaluation Method

A sensitivity was evaluated by the irradiation amount (μC/cm$^2$) necessary for reproducing a contact hole pattern of 0.20 μm.

Resolving Power Evaluation Method

The resolving power is shown by limiting resolving power in the irradiation amount necessary for reproducing the contact hole pattern of 0.20 μm.

TABLE 3

| Example (EB) | Sensitivity (μC/cm$^2$) | Resolving Power (μm) | Profile |
|---|---|---|---|
| 3 | 2 | 0.10 | Rectangle |
| 4 | 4 | 0.09 | Rectangle |
| 14 | 6 | 0.09 | Rectangle |
| 20 | 5 | 0.09 | Rectangle |
| 21 | 6 | 0.08 | Rectangle |
| 24 | 7 | 0.09 | Rectangle |
| 25 | 9 | 0.08 | Rectangle |
| 31 | 7 | 0.10 | Rectangle |

From the results shown in Table 3 described above, it can be seen that the compositions of the invention further form patterns of excellent rectangular profiles by an electron beam irradiation without forming a reversed taper profile caused by scattering specific to the electron beam irradiation, at a high sensitivity and a high resolving power.

As described above, the positive resist composition of the invention has an improved resolving power and an improved process allowability such as an exposure margin, a depth of focus, etc., in a lithography technique using an exposure light source of short wavelengths capable of super fine working and a positive chemically amplified resist. Also, even using an electron beam as the energy beam for exposure, the resist composition of the invention shows an excellent performance.

What is claimed is:

1. A positive resist composition comprising:
   (A) a compound generating a compound represented by the formula (I) below by irradiation with an actinic ray or a radiation; and
   (B) a resin having a group which is decomposed by the action of an acid to increase the solubility of the composition in an alkali developer:

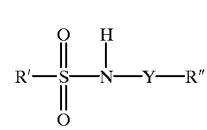

(I)

wherein, Y represents a single bond, —CO—, or —SO$_2$—; R' and R" are bonded to each other to form an alkylene group, an arylene group, or an aralkylene group, thereby, the structure of the formula (I) is in the form a ring.

2. The positive resist composition according to claim 1, which further comprises (D) a compound having a molecular weight of not larger than 3000, which is decomposed by the action of an acid to increase the solubility in an alkali developer.

3. The positive resist composition according to claim 1, wherein the pKa of the compound represented by the formula (I) is in the range of from −5 to 5.

4. The positive resist composition according to claim 1, wherein the resin (B) is a resin containing repeating structural units represented by the following formulae (II) and (III):

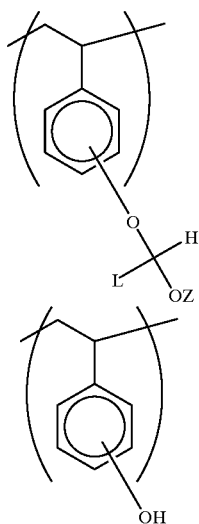

wherein L represents a hydrogen atom, a straight chain, branched, or cyclic alkyl group which may be substituted, or an aralkyl group which may be substituted; Z represents a straight chain, branched, or cyclic alkyl group which may be substituted or an aralkyl group which may be substituted; and Z and L may be bonded to each other to form a 5- or 6-membered ring.

5. The positive resist composition according to claim 4, wherein Z of the formula (II) is a substituted alkyl group or a substituted aralkyl group.

6. The positive resist composition according to claim 1, which further comprises (F) a nitrogen-containing basic compound and (G) at least one of a fluorine atom containing surfactant and a silicon atom containing surfactant.

7. The positive resist composition according to claim 1, which further comprises (C) a compound generating sulfonic acid by irradiation with an actinic ray or a radiation.

8. The positive resist composition according to claim 1, wherein formula (I) is a compound selected from the following compounds:

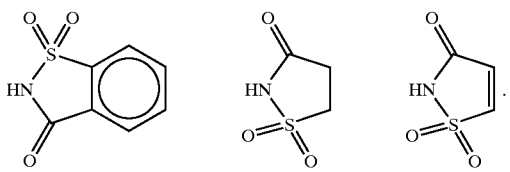

9. A positive resist composition comprising:
(A) a compound generating a compound represented by the formula (I) below by irradiation with an actinic ray or a radiation;

(D) a compound having a molecular weight of not larger than 3000, which is decomposed by the action of an acid to increase the solubility in an alkali developer; and
(E) an alkali-soluble resin:

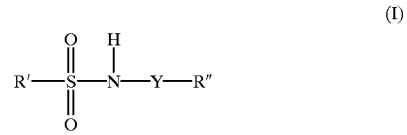

wherein, Y represents a single bond, —CO—, or —SO$_2$—; R' and R" are bonded to each other to form an alkylene group, an arylene group, or an aralkylene group, and, thereby, the structure of the formula (I) is in the form of ring.

10. The positive resist composition according to claim 9, wherein the pKa of the compound represented by the formula (I) is in the range of from −5 to 5.

11. The positive resist composition according to claim 9, which further comprises (F) a nitrogen-containing basic compound and (G) at least one of a fluorine atom containing surfactant and a silicon atom containing surfactant.

12. The positive resist composition according to claim 9, which further comprises (C) a compound generating sulfonic acid by irradiation with an actinic ray or a radiation.

13. The positive resist composition according to claim 9, wherein formula (I) is a compound selected from the following compounds:

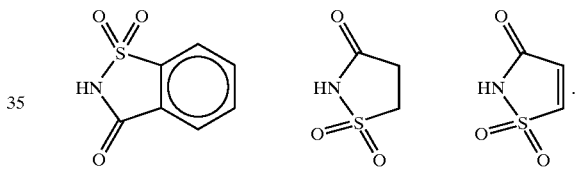

14. A sulfonium salt compound represented by the formula (IVa):

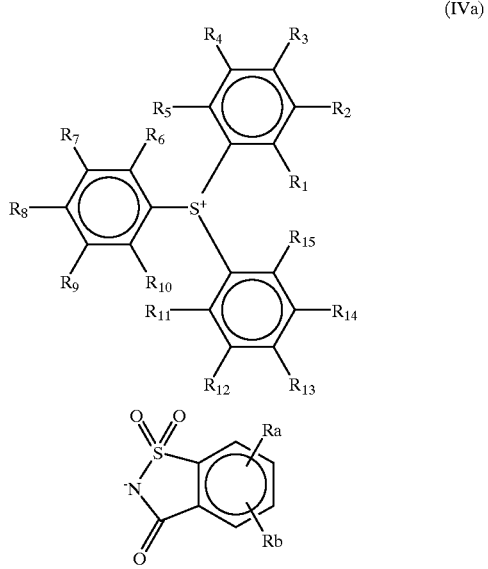

wherein, R$_1$ to R$_{15}$ each independently represents a hydrogen atom, a straight chain or branched alkyl group having from 1 to 5 carbon atoms, a cyclic alkyl group having from 3 to 8 carbon atoms, an alkoxy group having from 1 to 4 carbon atoms, a halogen atom, or —S—$R_{38}$ (wherein $R_{38}$ represents a straight chain or branched alkyl group having from 1 to 5 carbon atoms, a cyclic alkyl group having from 3 to 8 carbon atoms, or an aryl group having from 6 to 14 carbon atoms); Ra and Rb each independently represents a hydrogen atom, a halogen atom, an alkyl group having from 1 to 5 carbon atoms, an alkoxy group having from 1 to 5 carbon atoms, a nitro group, or a hydroxy group.

15. The sulfonium salt compound according to claim 14, wherein in the formula (IVa), $R_1$, $R_2$, $R_4$ to $R_7$, $R_9$ to $R_{12}$, $R_{14}$, $R_{15}$, Ra, and Rb each is a hydrogen atom, and $R_3$, $R_8$, and $R_{13}$ each independently represents a hydrogen atom, an alkyl group having from 1 to 5 atoms, an alkoxy group having from 1 to 5 carbon atoms, or a halogen atom.

16. A sulfonium salt compound represented by the formula (Va):

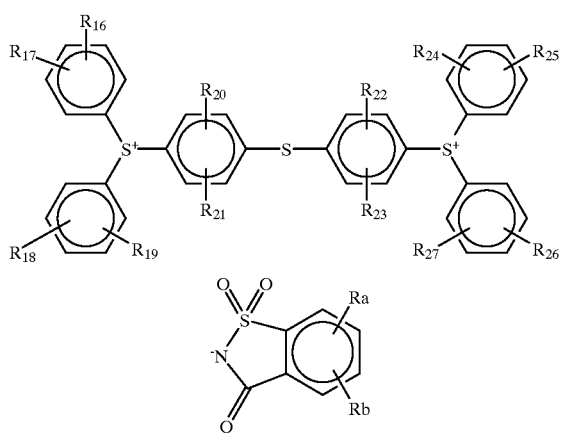

(Va)

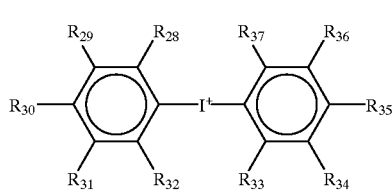

wherein $R_{16}$ to $R_{27}$ each independently represents a hydrogen atom, a straight chain or branched alkyl group having from 1 to 5 carbon atoms, a cyclic alkyl group having from 3 to 8 carbon atoms, an alkoxy group having from 1 to 4 carbon atoms, a halogen atom, or —S—$R_{38}$ (wherein $R_{38}$ represents a straight chain or branched alkyl group having from 1 to 5 carbon atoms, a cyclic alkyl group having from 3 to 8 carbon atoms, or an aryl group having from 6 to 14 carbon atoms); Ra and Rb each independently represents a hydrogen atom, a halogen atom, an alkyl group having from 1 to 5 carbon atoms, an alkoxy group having from 1 to 5 carbon atoms, a nitro group, or a hydroxy group.

17. The sulfonium salt compound according to claim 16, wherein in the formula (Va), $R_{16}$ to $R_{27}$, Ra, and Rb each is a hydrogen atom.

18. An iodonium salt compound represented by the formula (VIa):

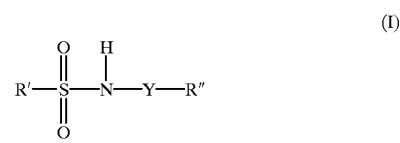

(VIa)

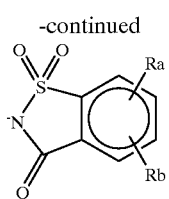

wherein $R_{28}$ to $R_{37}$ each independently represents a hydrogen atom, a straight chain or branched alkyl group having from 1 to 5 carbon atoms, a cyclic alkyl group having from 3 to 8 carbon atoms, an alkoxy group having from 1 to 4 carbon atoms, a halogen atom, or —S—$R_{38}$ (wherein $R_{38}$ represents a straight chain or branched alkyl group having from 1 to 5 carbon atoms, a cyclic alkyl group having from 3 to 8 carbon atoms, or an aryl group having from 6 to 14 carbon atoms); Ra and Rb each independently represents a hydrogen atom, a halogen atom, an alkyl group having from 1 to 5 carbon atoms, an alkoxy group having from 1 to 5 carbon atoms, a nitro group, or a hydroxy group.

19. The iodonium salt compound according to claim 18, wherein in the formula (VIa), $R_{28}$, $R_{29}$, $R_{31}$ to $R_{34}$, $R_{36}$, $R_{37}$, Ra, and Rb each is a hydrogen atom, and $R_{30}$ and $R_{35}$ each independently a hydrogen atom or an alkyl group having from 1 to 5 carbon atoms.

20. A positive resist composition comprising:
(A) a compound generating a compound represented by the formula (I) below by irradiation with an actinic ray or a radiation, wherein said compound generating a compound represented by the formula (I) is a sulfonium salt or an iodonium salt of the anion formed by a dissociation of N—H in the compound represented by the formula (I); and
(B) a resin having a group which is decomposed by the action of an acid to increase the solubility of the composition in an alkali developer:

$$R'-\overset{O}{\underset{O}{\overset{\|}{S}}}-\overset{H}{\underset{}{N}}-Y-R''$$ (I)

wherein, Y represents a single bond, —CO—, or —SO$_2$—; R' and R", which may be the same or different, each represents a straight chain, branched, or cyclic alkyl group which may be substituted, an aryl group which may be substituted, an aralkyl group which may be substituted, or a camphor group; R' and R" may be bonded to each other to form an alkylene group, an arylene group, or an aralkylene group, thereby, the structure of the formula (I) may form a ring; and when Y is a —CO— group, R" may be a hydroxy group or an alkoxy group.

21. The positive resist composition according to claim 20, which further comprises (D) a compound having a molecular weight of not larger than 3000, which is decomposed by the action of an acid to increase the solubility in an alkali developer.

22. The positive resist composition according to claim 20, wherein the resin (B) is a resin containing repeating structural units represented by the following formulae (II) and (III):

(II)

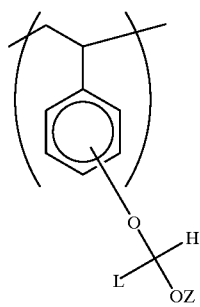

(III)

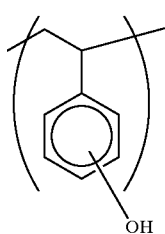

(V)

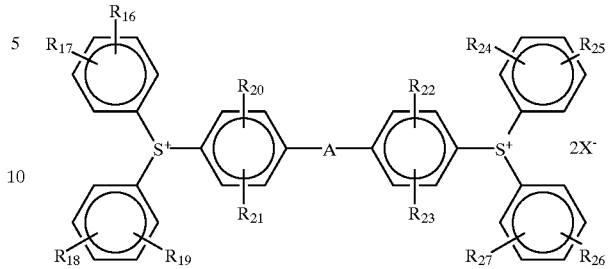

(VI)

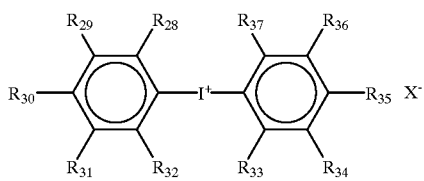

wherein L represents a hydrogen atom, a straight chain, branched, or cyclic alkyl group which may be substituted, or an aralkyl group which may be substituted; Z represents a straight chain, branched, or cyclic alkyl group which may be substituted or an aralkyl group which may be substituted; and Z and L may be bonded to each other to form a 5- or 6-membered ring.

23. The positive resist composition according to claim 22, wherein Z of the formula (II) is a substituted alkyl group or a substituted aralkyl group.

24. The positive resist composition according to claim 20, which further comprises (F) a nitrogen-containing basic compound and (G) at least one of a fluorine atom containing surfactant and a silicon atom containing surfactant.

25. The positive resist composition according to claim 20, wherein the compound (A) is a compound having a structure represented by one of the following formulae (IV) to (VI):

(IV)

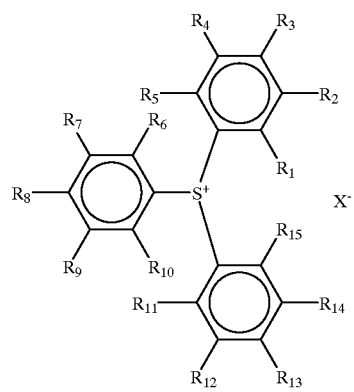

wherein $R_1$ to $R_{37}$ each independently represents a hydrogen atom, a straight chain, branched, or cyclic alkyl group, a straight chain, branched, or cyclic alkoxy group, a hydroxy group, a halogen atom, or a —S—$R_{38}$ group (wherein $R_{38}$ represents a straight chain, branched, or cyclic alkyl group or an aryl group); $X^-$ represents the anion formed by the dissociation of NH in the compound represented by the formula (I); A represents a single bond, a sulfur atom, an oxygen atom, or a methylene group.

26. The positive resist composition according to claim 25, wherein $X^-$ in the formulae (IV) to (VI) contains the following structure:

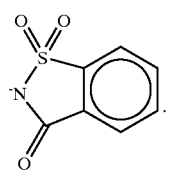

27. The positive resist composition according to claim 20, which further comprises (C) a compound generating sulfonic acid by irradiation with an actinic ray or a radiation.

28. A positive resist composition comprising:
(A) a compound generating a compound represented by the formula (I) below by irradiation with an actinic ray or a radiation, wherein said compound generating a compound represented by the formula (I) is a sulfonium salt or an iodonium salt of the anion formed by a dissociation of N—H in the compound represented by the formula (I)
(D) a compound having a molecular weight of not larger than 3000, which is decomposed by the action of an acid to increase the solubility in an alkali developer; and (E) an alkali-soluble resin:

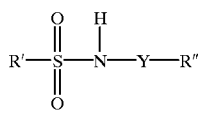
(I)

wherein, Y represents a single bond, —CO—, or —SO$_2$—; R' and R", which may be the same or different, each represents a straight chain, branched, or cyclic alkyl group which may be substituted, an aryl group which may be substituted, an aralkyl group which may be substituted, or a camphor group; R' and R" may be bonded to each other to form an alkylene group, an arylene group, or an aralkylene group, and, thereby, the structure of the formula (I) may form a ring; and when Y is a —CO— group, R" may be a hydroxy group or an alkoxy group.

29. The positive resist composition according to claim 28, which further comprises (F) a nitrogen-containing basic compound and (G) at least one of a fluorine atom containing surfactant and a silicon atom containing surfactant.

30. The positive resist composition according to claim 28, wherein the compound (A) is a compound having a structure represented by one of the following formulae (IV) to (VI):

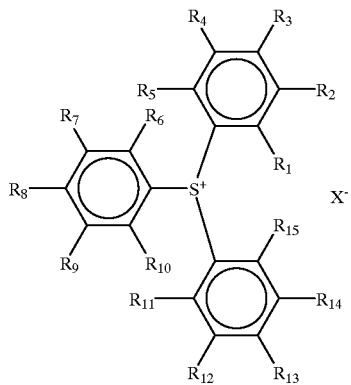
(IV)

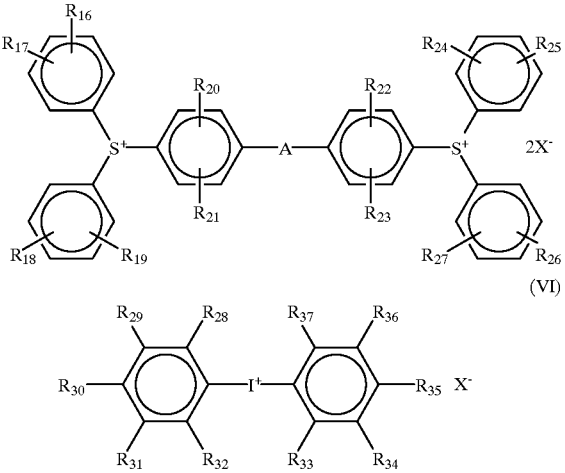
(V)

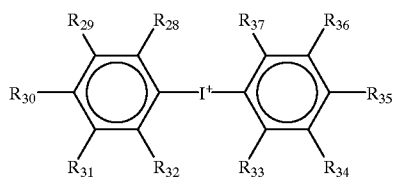
(VI)

wherein R$_1$ to R$_{37}$ each independently represents a hydrogen atom, a straight chain, branched, or cyclic alkyl group, a straight chain, branched, or cyclic alkoxy group, a hydroxy group, a halogen atom, or a —S—R$_{38}$ group (wherein R$_{38}$ represents a straight chain, branched, or cyclic alkyl group or an aryl group); X$^-$ represents an anion of the compound represented by the formula (I); A represents a single bond, a sulfur atom, an oxygen atom, or a methylene group.

31. The positive resist composition according to claim 30, wherein X$^-$ in the formulae (IV) to (VI) contains the following structure:

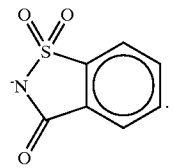

32. The positive resist composition according to claim 28, which further comprises (C) a compound generating sulfonic acid by irradiation with an actinic ray or a radiation.

* * * * *